United States Patent
Takeshima et al.

(10) Patent No.: US 11,710,230 B2
(45) Date of Patent: Jul. 25, 2023

(54) MEDICAL DATA PROCESSING APPARATUS AND MEDICAL IMAGE DIAGNOSTIC APPARATUS

(71) Applicant: Canon Medical Systems Corporation, Otawara (JP)

(72) Inventors: Hidenori Takeshima, Kawasaki (JP); Masanori Ozaki, Hachioji (JP); Hideaki Kutsuna, Kawasaki (JP); Kyoichiro Aoki, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 124 days.

(21) Appl. No.: 16/925,559

(22) Filed: Jul. 10, 2020

(65) Prior Publication Data

US 2021/0042913 A1 Feb. 11, 2021

(30) Foreign Application Priority Data

Aug. 9, 2019 (JP) .................................. 2019-147717

(51) Int. Cl.
*G06T 7/00* (2017.01)
*G16H 30/40* (2018.01)
*G16H 30/20* (2018.01)
*G16H 50/20* (2018.01)

(52) U.S. Cl.
CPC ............ *G06T 7/0012* (2013.01); *G16H 30/20* (2018.01); *G16H 30/40* (2018.01); *G16H 50/20* (2018.01); *G06T 2207/10016* (2013.01); *G06T 2207/10088* (2013.01); *G06T 2207/20081* (2013.01)

(58) Field of Classification Search
None
See application file for complete search history.

(56) References Cited

U.S. PATENT DOCUMENTS

| | | | | |
|---|---|---|---|---|
| 6,301,440 B1* | 10/2001 | Bolle | .................. | H04N 5/23222 396/128 |
| 2010/0183208 A1* | 7/2010 | Kondo | .................... | G16H 30/20 382/128 |
| 2018/0144465 A1* | 5/2018 | Hsieh | ....................... | G06N 3/08 |
| 2018/0144466 A1* | 5/2018 | Hsieh | ..................... | G06T 7/0012 |
| 2018/0322629 A1* | 11/2018 | Hu | ......................... | G06K 9/6232 |
| 2018/0349759 A1* | 12/2018 | Isogawa | ................ | G06N 3/0481 |

FOREIGN PATENT DOCUMENTS

| | | |
|---|---|---|
| JP | 5-61973 A | 3/1993 |
| JP | 2002-10135 A | 1/2002 |
| JP | 2013-176409 A | 9/2013 |
| JP | 2017-501787 | 1/2017 |

OTHER PUBLICATIONS

Office Action dated Apr. 25, 2023 in Japanese Application No. 2019-147717 filed Aug. 9, 2019.

\* cited by examiner

*Primary Examiner* — Vu Le
*Assistant Examiner* — Courtney Joan Nelson
(74) *Attorney, Agent, or Firm* — Oblon, McClelland, Maier & Neustadt, L.L.P.

(57) ABSTRACT

According to one embodiment, a medical data processing apparatus includes processing circuitry. The processing circuitry acquires medical data, and generates an imaging parameter by inputting the medical data to a trained model, the imaging parameter being a parameter of a medical image diagnostic apparatus with respect to the medical data, the trained model being trained to generate an imaging parameter of the medical image diagnostic apparatus based on medical data.

12 Claims, 15 Drawing Sheets

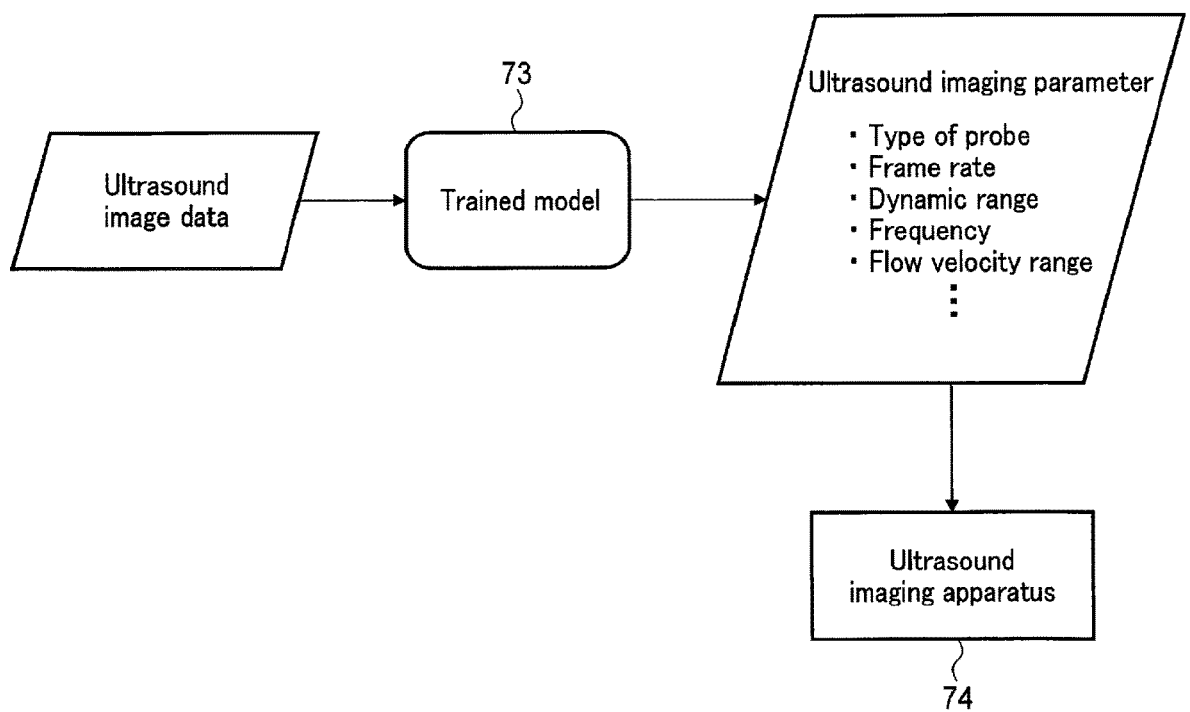
F I G. 16

MEDICAL DATA PROCESSING APPARATUS AND MEDICAL IMAGE DIAGNOSTIC APPARATUS

CROSS-REFERENCE TO RELATED APPLICATION

This application is based upon and claims the benefit of priority from Japanese Patent Application No. 2019-147717, filed Aug. 9, 2019, the entire contents of which are incorporated herein by reference.

FIELD

Embodiments described herein relate generally to a medical data processing apparatus and a medical image diagnostic apparatus.

BACKGROUND

Conventionally, in a medical image diagnostic apparatus, when a user executes medical imaging, for example, an imaging parameter at the time of shipment, an imaging parameter used in the past, or an imaging parameter described in a textbook or a paper is used. Furthermore, in a case where a medical image and an imaging parameter are associated with each other, a user can select a medical image of a desired aspect, and use an imaging parameter associated with the selected medical image.

However, in some cases, a medical image may not be associated with an imaging parameter. In such case, it is difficult for the user to estimate the parameter used for the imaging.

BRIEF DESCRIPTION OF THE DRAWINGS

FIG. 16 shows a first example of input/output of a trained model used in a generating function of FIG. 15, and an ultrasound diagnostic apparatus of an output destination.

DETAILED DESCRIPTION

Figure 1:
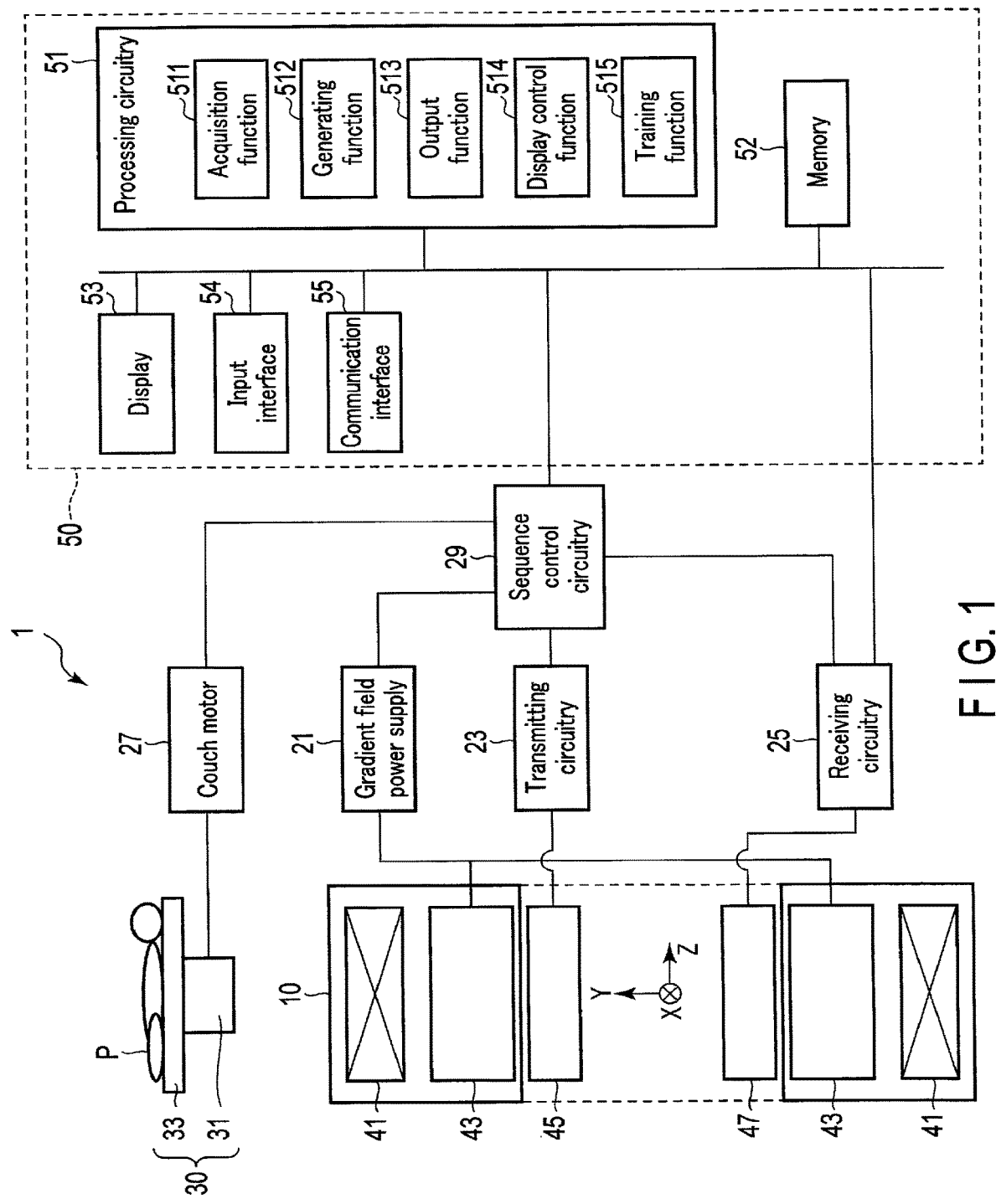
FIG. 1 shows a configuration of a magnetic resonance imaging apparatus according to a first embodiment.

In general, according to one embodiment, a medical data processing apparatus includes processing circuitry. The processing circuitry acquires medical data, and generates an imaging parameter by inputting the medical data to a trained model, the imaging parameter being a parameter of a medical image diagnostic apparatus with respect to the medical data, the trained model being trained to generate an imaging parameter of the medical image diagnostic apparatus based on medical data.

Hereinafter, embodiments of the medical data processing apparatus and the medical image diagnostic apparatus will be explained in detail with reference to the drawings.

The medical data processing apparatus according to the present embodiments is a computer or a processor that processes medical data acquired by a medical apparatus, etc., or medical data stored in an external storage apparatus, etc. As the medical apparatus according to the present embodiments, the medical image diagnostic apparatus or biological information measuring equipment can be used. The medical image diagnostic apparatus acquires a medical image by performing medical imaging on a subject by various imaging principles. Examples of the medical image diagnostic apparatus include a magnetic resonance imaging apparatus, an X-ray computed tomography apparatus, an ultrasound diagnostic apparatus, a nuclear medicine diagnostic apparatus, an X-ray diagnostic apparatus, an optical coherence tomography apparatus, an optical ultrasonic apparatus, and an endoscope. The biological information measuring equipment acquires waveform data relating to biological information of a subject by various measurement principles. Examples of the biological information measuring equipment include an automatic analysis apparatus, an electrocardiograph, a spirometer, a sphygmomanometer, and a pulse oximeter.

The medical data according to the present embodiments includes medical image data. The medical image data is acquired from, for example, a medical image diagnostic apparatus or a picture archiving and communication system (PACS). However, the acquisition source may be any source. As the medical image data, there are magnetic resonance (MR) image data, map image data based on MR imaging, CT image data, ultrasound image data, X-ray image data, and the like. The map image data will be described later. The medical image data may be a digital imaging and communication in medicine (DICOM) format or a non-DICOM format.

The medical data according to the present embodiments may include medical image-like image data. The medical image-like image data is, for example, image data obtained by photographing or reading a medical image printed on paper or recorded on film. Specifically, the medical image-like image data is image data obtained by clipping medical image data, image data acquired by photographing a medical image printed on paper by a camera, or image data captured by an optical scanner, etc. As the medical image-like image data, there are MR image-like image data, CT image-like image data, ultrasound image-like image data, and X-ray image-like image data, etc.

The medical data according to the present embodiments may include supplementary data relating to the image data. The supplementary data is, for example, a known imaging parameter, DICOM data, and label data. The imaging parameter is, for example, a parameter relating to imaging of the medical image diagnostic apparatus when acquiring medical image data. The DICOM data is, for example, tag data relating to an imaging parameter that is attached to medical image data in DICOM format. The label data is, for example, data in one-hot vector format, in which the presence of an element is corresponded to "zero" or "one".

The imaging parameter may include information relating to the medical image diagnostic apparatus. The information relating to the medical image diagnostic apparatus is, for example, information on static magnetic field strength (for example, 1.5 T, 3 T, and 7 T) in the case of the magnetic resonance imaging apparatus, information on the number of rows of multi-slices (for example, 64 rows and 320 rows) in the case of the X-ray computed tomography apparatus, and information on the type of probe (for example, a convex probe, a sector probe, a linear probe, and a 3D probe) in the case of the ultrasound diagnostic apparatus.

The medical data processing apparatus according to the present embodiments may be a computer or a processor mounted on the medical apparatus, or may be a computer or a processor that is separate from the medical apparatus. For the purpose of providing detailed explanations, the medical data processing apparatus according to a first embodiment is assumed as a computer mounted on the magnetic resonance imaging apparatus, the medical data processing apparatus according to a second embodiment is assumed as a computer mounted on the X-ray computed tomography apparatus, and the medical data processing apparatus according to a third embodiment is assumed as a computer mounted on the ultrasound diagnostic apparatus.

First Embodiment

FIG. 1 shows a configuration of a magnetic resonance imaging apparatus according to a first embodiment. As shown in FIG. 1, a magnetic resonance imaging apparatus 1 includes a gantry 10, a couch 30, a gradient field power supply 21, transmitting circuitry 23, receiving circuitry 25, a couch motor 27, sequence control circuitry 29, and a medical data processing apparatus 50.

The gantry 10 includes a static field magnet 41 and a gradient field coil 43. The static field magnet 41 and the gradient field coil 43 are accommodated in the housing of the gantry 10. The housing of the gantry 10 is formed with a bore having a hollow shape. A transmitting coil 45 and a receiving coil 47 are disposed in the bore of the gantry 10.

The static field magnet 41 has a hollow substantially cylindrical shape and generates a static magnetic field inside a substantially cylindrical interior. Examples of the static field magnet 41 used include a permanent magnet, a superconducting magnet or a normal conducting magnet. Here, a central axis of the static field magnet 41 is defined as a Z axis, an axis vertically perpendicular to the Z axis is defined as a Y axis, and an axis horizontally perpendicular to the Z axis is defined as an X axis. The X axis, the Y axis and the Z axis constitute an orthogonal three-dimensional coordinate system.

The gradient field coil 43 is a coil unit attached to the inside of the static field magnet 41 and formed in a hollow substantially cylindrical shape. The gradient field coil 43 receives supply of a current from the gradient field power supply 21 to generate a gradient field. More specifically, the gradient field coil 43 has three coils corresponding to the X axis, the Y axis, and the Z axis orthogonal to each other. The three coils form a gradient field in which the magnetic field strength changes along the X axis, the Y axis, and the Z axis respectively. The gradient fields respectively along the X axis, the Y axis, and the Z axis are combined to form slice selection gradient fields Gs, phase encoding gradient fields Gp, and frequency encoding gradient fields Gr that are orthogonal to each other in arbitrary directions. The slice selection gradient fields Gs are used to determine the imaging cross section (slice) arbitrarily. The phase encoding gradient fields Gp are used to vary the phase of the magnetic resonance signal (hereinafter referred to as the MR signal) according to a spatial position. The frequency encoding gradient fields Gr are used to vary the frequency of the MR signal according to the spatial position. It should be noted that in the following description, it is assumed that the direction of gradient of the slice selection gradient fields Gs corresponds to the Z axis, the direction of gradient of the phase encoding gradient fields Gp corresponds to the Y axis, and the direction of gradient of the frequency encoding gradient fields Gr corresponds to the X axis.

The gradient field power supply 21 supplies a current to the gradient field coil 43 in accordance with a sequence control signal from the sequence control circuitry 29. The gradient field power supply 21 supplies a current to the gradient field coil 43 and causes the gradient field coil 43 to generate a gradient field along each of the X axis, Y axis, and Z axis. The gradient field is superimposed on the static magnetic field formed by the static field magnet 41 and applied to a subject P.

The transmitting coil 45 is disposed, for example, inside the gradient field coil 43, and receives supply of a current from the transmitting circuitry 23 to generate a high frequency magnetic field pulse (hereinafter referred to as an RF magnetic field pulse).

The transmitting circuitry 23 supplies a current to the transmitting coil 45 in order to apply an RF magnetic field pulse for exciting a target proton in the subject P to the subject P via the transmitting coil 45. The RF magnetic field pulse oscillates at a resonance frequency specific to the target proton to excite the target proton. An MR signal is generated from the excited target proton and detected by the receiving coil 47. The transmitting coil 45 is, for example, a whole-body coil (WB coil). The whole-body coil may be used as a transmitting and receiving coil.

The receiving coil 47 receives the MR signal emitted from the target proton present in the subject P under an action of the RF magnetic field pulse. The receiving coil 47 has a plurality of receiving coil elements capable of receiving the MR signal. The received MR signal is supplied to the receiving circuitry 25 via wire or wireless means. Although not shown in FIG. 1, the receiving coil 47 has a plurality of receiving channels implemented in parallel. The receiving channels each include receiving coil elements that receive the MR signal, an amplifier that amplifies the MR signal, and the like. The MR signal is output for each receiving channel. The total number of the receiving channels and the total number of the receiving coil elements may be the same, or the total number of the receiving channels may be larger or smaller than the total number of the receiving coil elements.

The receiving circuitry 25 receives the MR signal generated from the excited target proton via the receiving coil 47. The receiving circuitry 25 processes the received MR signal to generate a digital MR signal. The digital MR signal can be expressed in k-space defined by a spatial frequency. Therefore, hereinafter, the digital MR signal is referred to as k-space data. The k-space data is supplied to the medical data processing apparatus 50 via wire or wireless.

It should be noted that the transmitting coil 45 and the receiving coil 47 described above are merely examples. Instead of the transmitting coil 45 and the receiving coil 47, a transmitting and receiving coil having a transmitting function and a receiving function may be used. Also, the transmitting coil 45, the receiving coil 47, and the transmitting and receiving coil may be combined.

The couch 30 is installed adjacent to the gantry 10. The couch 30 has a table top 33 and a base 31. The subject P is placed on the table top 33. The base 31 slidably supports the table top 33 respectively along the X axis, the Y axis, and the Z axis. The couch motor 27 is accommodated in the base 31. The couch motor 27 moves the table top 33 under the control of the sequence control circuitry 29. The couch motor 27 may, for example, include any motor such as a servo motor or a stepping motor.

The sequence control circuitry 29 has a processor such as a central processing unit (CPU) or a micro processing unit (MPU) and a memory such as a read only memory (ROM) or a random access memory (RAM) as hardware resources. The sequence control circuitry 29 synchronously controls the gradient field power supply 21, the transmitting circuitry 23, and the receiving circuitry 25 based on an imaging protocol determined by processing circuitry 51, executes MR imaging on the subject P in accordance with a pulse sequence corresponding to the imaging protocol, and acquires the k-space data relating to the subject P.

As shown in FIG. 1, the medical data processing apparatus 50 is a computer having processing circuitry 51, a memory 52, a display 53, an input interface 54, and a communication interface 55.

The processing circuitry 51 includes, as hardware resources, a processor such as a CPU. The processing circuitry 51 functions as the core of the magnetic resonance imaging apparatus 1. For example, by executing various programs, the processing circuitry 51 realizes an acquisition function 511, a generating function 512, an output function 513, a display control function 514, and a training function 515. It should be noted that, although not shown, by executing various programs, the processing circuitry 51 realizes an imaging protocol setting function, an image reconstruction function, and an image processing function.

In the imaging protocol setting function, the processing circuitry 51 sets an imaging protocol relating to MR imaging by a user instruction via the input interface 54 or automatically. The imaging protocol is a set of various MR imaging parameters related to MR imaging. The MR imaging parameter will be described later.

In the image reconstruction function, the processing circuitry 51 reconstructs an MR image based on k-space data acquired by various scans. A reconstruction method is not limited in particular.

In the image processing function, the processing circuitry 51 performs various types of image processing on the MR image. For example, the processing circuitry 51 performs image processing such as volume rendering, surface rendering, pixel value projection processing, multi-planer reconstruction (MPR) processing, and curved MPR (CPR) processing.

In the acquisition function 511, the processing circuitry 51 acquires medical data from the PACS, etc. by the user's instruction. In the present embodiment, the processing circuitry 51 acquires, for example, MR image data, map image data, and MR image-like image data.

Furthermore, the processing circuitry 51 may acquire supplementary data.

In the generating function 512, the processing circuitry 51 applies a trained model to medical data and generates an imaging parameter of a medical image diagnostic apparatus relating to the medical data. In other words, the processing circuitry 51 generates an imaging parameter by inputting the medical data to a trained model, the imaging parameter being a parameter of a medical image diagnostic apparatus with respect to the medical data, the trained model being trained to generate an imaging parameter of the medical image diagnostic apparatus based on medical data. The trained model is, for example, a machine learning model that is trained based on medical data and an imaging parameter of a medical image diagnostic apparatus relating to the medical data, prepared in advance. It should be noted that, in the present embodiment, in the case where medical image data is included in the medical data, the medical image data is associated with the medical image diagnostic apparatus. Furthermore, in the case where medical image-like image data is included in the medical data, the image data is associated with a medical image apparatus that acquired the medical image.

In the present embodiment, for example, the processing circuitry 51 applies a trained model to the MR image data and generates an MR imaging parameter relating to the MR image data. In other words, the processing circuitry 51 generates an MR imaging parameter by inputting the MR image data to a trained model, the MR imaging parameter being a parameter of a magnetic resonance imaging apparatus with respect to the MR image data, the trained model being trained to generate an MR imaging parameter of the magnetic resonance imaging apparatus based on an MR image data. Here, the trained model is, for example, a machine learning model that is trained based on MR image data and an MR imaging parameter (an MR imaging parameter of a magnetic resonance imaging apparatus) that is used when acquiring k-space data corresponding to the MR image data, prepared in advance.

The machine learning model according to the present embodiment is assumed, typically, to be a deep neural network (DNN), which is a multilayered network model simulating a neural circuit of a brain of a living creature. The DNN includes a parameterized synthesis function defined by a combination of a plurality of adjustable functions and parameters.

In the output function 513, the processing circuitry 51 outputs the imaging parameter of the medical image diagnostic apparatus generated by the generating function 512 to an imaging apparatus. The term imaging apparatus refers to the units and circuitry performing medical imaging in the medical image diagnostic apparatus. The processing circuitry 51 may convert the imaging parameter into an imaging parameter in accordance with an imaging apparatus of the output destination. The imaging apparatus may be identical to the medical image diagnostic apparatus. In the present embodiment, for example, the processing circuitry 51 outputs the MR imaging parameter of the magnetic resonance imaging apparatus generated by the generating function 512 to an MR imaging apparatus.

In the display control function 514, the processing circuitry 51 displays various types of information on the display 53. For example, the processing circuitry 51 displays the imaging parameter of the medical image diagnostic apparatus, etc. output by the output function 513 on the display 53. In the present embodiment, the processing circuitry 51 displays, for example, a reference MR image used as input data, the MR imaging parameter of the magnetic resonance imaging apparatus output by the output function 513, and an MR image (output MR image) of the subject P imaged by using the MR imaging parameter on the display 53.

In the training function 515, the processing circuitry 51 generates a trained model that is trained based on medical data and an imaging parameter of a medical image diagnostic apparatus relating to the medical data, prepared in advance. For example, the processing circuitry 51 generates the trained model by supervised training using the medical data and the imaging parameter of the medical image diagnostic apparatus relating to the medical data as supervising data. When training, reinforcement training may also be used in combination.

In the present embodiment, for example, the processing circuitry 51 generates a machine learning model that is trained based on MR image data and an MR imaging parameter relating to the MR image data, prepared in advance. For example, the processing circuitry 51 generates the trained model by supervised training that uses the MR image data and the MR imaging parameter relating to the MR image data as supervising data.

In summary, the medical data processing apparatus acquires medical data, and generates an imaging parameter by inputting the medical data to a trained model, the imaging parameter being a parameter of a medical image diagnostic apparatus with respect to the medical data, the trained model being trained to generate an imaging parameter of the medical image diagnostic apparatus based on medical data. Therefore, the present medical data processing apparatus is capable of estimating an imaging parameter from medical data of which an imaging parameter is unknown so that, for example, a user may set an optimal imaging parameter of the medical image diagnostic apparatus. The medical data includes at least the image data.

The memory 52 is a storage apparatus such as a hard disk drive (HDD), a solid state drive (SSD), an integrated circuitry storage apparatus or the like that stores various information. The memory 52 may also be a drive apparatus or the like that reads and writes various information from and to a portable storage medium such as a CD-ROM drive, a DVD drive, a flash memory, and the like. For example, the memory 52 stores k-space data, MR image data, map image data, various programs, and the like.

The display 53 displays various types of information by the display control function 514. For example, the display 53 displays the imaging parameter of the medical image diagnostic apparatus output by the output function 513. In the present embodiment, the display 53 displays, for example, the reference MR image, the MR imaging parameter, the output MR image, and the like. Examples of displays 53 that can be used as appropriate include a CRT display, a liquid crystal display, an organic EL display, an LED display, a plasma display, or any other display known in the art.

The input interface 54 includes an input device that receives various commands from the user. Examples of the input device that can be used are a keyboard, a mouse, various switches, a touch screen, a touch pad, and the like. It should be noted that the input device is not limited to those having physical operation parts such as a mouse and keyboard. For example, the input interface 54 could also include electrical signal processing circuitry that receives an electrical signal corresponding to an input operation from an external input device provided separately from the magnetic resonance imaging apparatus 1, and outputs the received electrical signal to various types of circuitry.

The communication interface 55 is an interface connecting the magnetic resonance imaging apparatus 1 with a workstation, PACS, a hospital information system (HIS), a radiology information system (RIS), and the like via a local area network (LAN) or the like. A network IF transmits and receives various types of information to and from the connected workstation, PACS, HIS, and RIS.

It should be noted that the above configuration is merely an example, and the present invention is not limited thereto. For example, the sequence control circuitry 29 may be incorporated into the medical data processing apparatus 50. Also, the sequence control circuitry 29 and the processing circuitry 51 may be mounted on the same substrate. The sequence control circuitry 29, the gradient field power supply 21, the transmitting circuitry 23 and the receiving circuitry 25 may be mounted on a single control apparatus different from the medical data processing apparatus 50 or may be distributed and mounted on a plurality of apparatuses.

Hereinafter, an operation example of the magnetic resonance imaging apparatus 1 according to the present embodiment will be explained.

Figure 2:
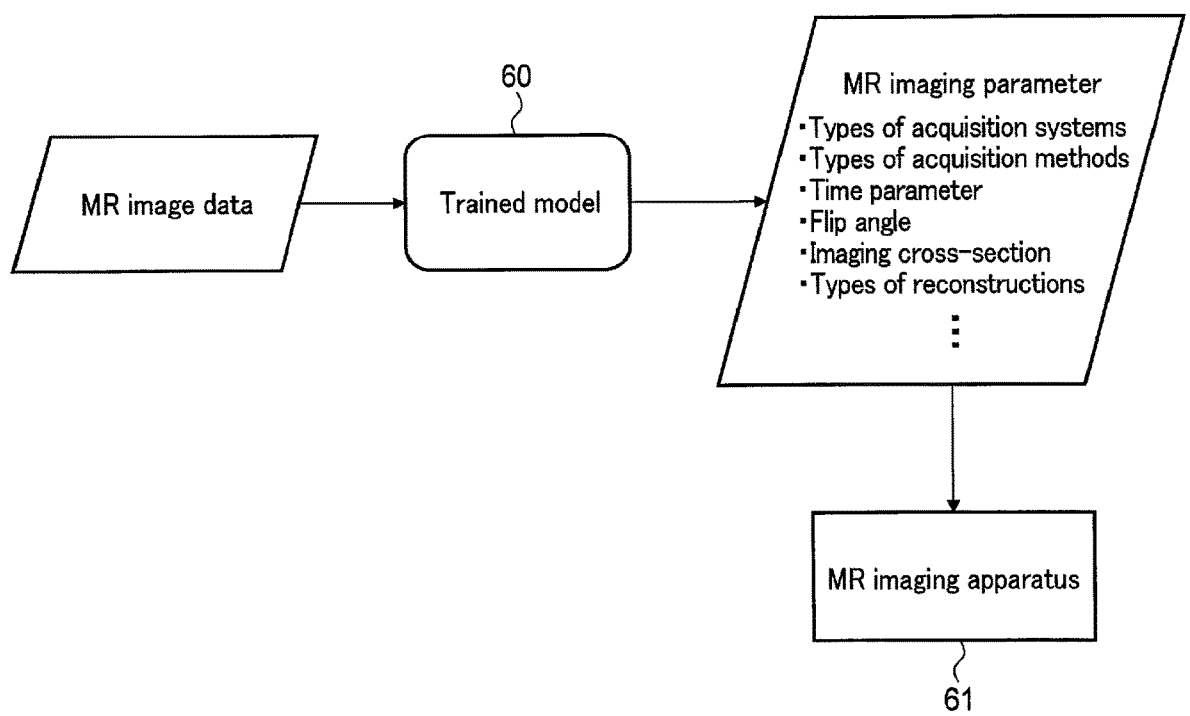
FIG. 2 shows a first example of input/output of a trained model used in a generating function of FIG. 1, and an MR imaging apparatus of an output destination.

FIG. 2 shows a first example of input/output of the trained model used in the generating function of FIG. 1, and an imaging apparatus of an output destination. The processing circuitry 51 acquires MR image data by the acquisition function 511. By the generating function 512, the processing circuitry 51 applies a trained model 60 to the MR image data and generates an MR imaging parameter relating to the MR image data. By the output function 513, the processing circuitry 51 outputs the MR imaging parameter to an MR imaging apparatus 61.

The MR imaging parameter is a parameter relating to imaging of the magnetic resonance imaging apparatus when acquiring the MR image data. Furthermore, the MR imaging parameter may include information relating to the magnetic resonance imaging apparatus.

Examples of MR imaging parameters include types of acquisition systems, types of acquisition methods, a time parameter, a flip angle, an imaging cross-section, types of reconstructions, FOV, a matrix size, a slice thickness, the number of phase encoding steps, a scan option, and the like.

The types of acquisition systems include, for example, information on static magnetic field strength and information on an acquisition coil (for example, a head coil and a body coil). The types of acquisition methods include, for example, information on types of sequences (for example, spin echo (SE), fast spin echo (FSE), echo planar (EP), inversion recovery (IR), gradient echo (GRE), and balanced steady state free precession (bSSFP)). The time parameter includes, for example, information on a time parameter (for example, an echo time (TE) and a repeating time (TR)) that sets the characteristic of the pulse sequence. The types of reconstructions include, for example, information on a reconstruction method attributable to an imaging technique (for example, parallel imaging (PI) and compressed sensing (CS)) and information on a reconstruction method using deep learning (deep learning reconstruction (DLR)). The matrix size includes, for example, information on the number of samples in an XY direction of an image and information on spatial resolution. The scan option includes, for example, information on settings relating to an individual sequence (for example, spatial presaturation (SP), fat saturation (FS), pre-inversion recovery (PreIR)), and number of shots).

Figure 3:
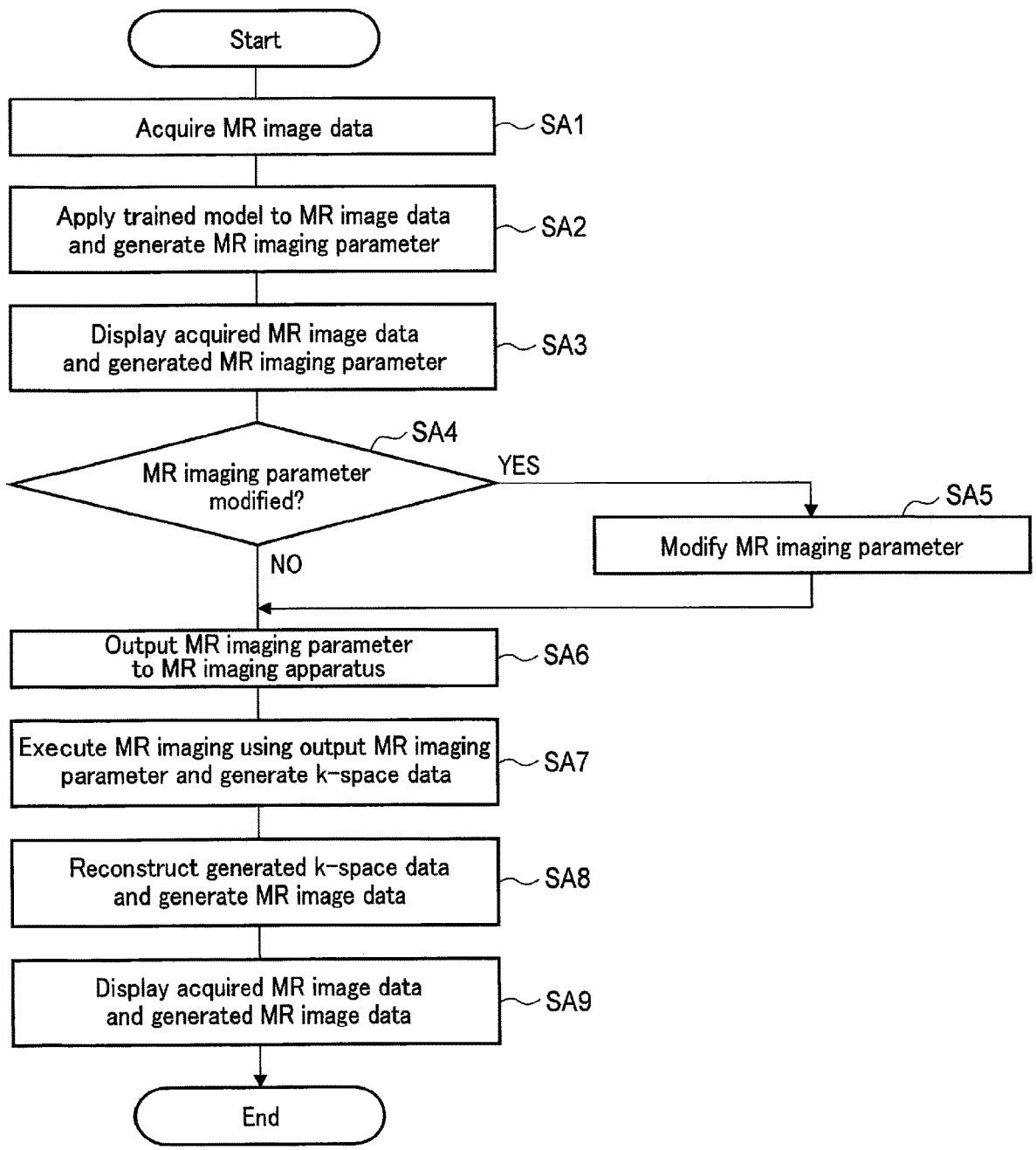
FIG. 3 is a flowchart for explaining a series of events including MR imaging parameter estimation processing in the first embodiment relating to FIG. 2.

FIG. 3 is a flowchart for explaining a series of events including MR imaging parameter estimation processing in the first embodiment relating to FIG. 2. For example, the flowchart of FIG. 3 starts by the processing circuitry 51 executing an MR imaging parameter estimation program, which is triggered by an instruction to activate an application relating to the MR imaging parameter estimation processing input by a user.

(Step SA1)

When the MR imaging parameter estimation program is executed, the processing circuitry 51 executes the acquisition function 511. When the acquisition function 511 is executed, the processing circuitry 51 acquires MR image data assigned by the user.

(Step SA2)

After acquiring the MR image data, the processing circuitry 51 executes the generating function 512. When the generating function 512 is executed, the processing circuitry 51 applies a trained model to the MR image data and generates an MR imaging parameter.

(Step SA3)

After generating the MR imaging parameter, the processing circuitry 51 executes the display control function 514. When the display control function 514 is executed, the processing circuitry 51 displays the acquired MR image data (reference MR image) and the generated MR imaging parameter (estimated MR imaging parameter) on the display 53.

Figure 4:
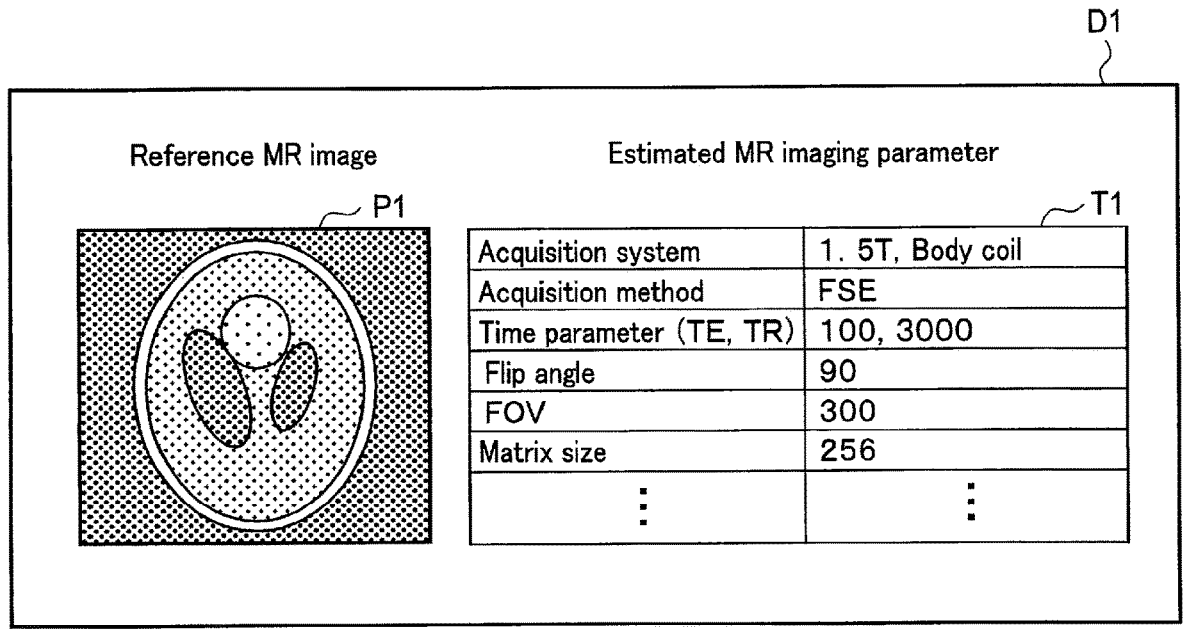
FIG. 4 shows an example of a display screen of a reference MR image and an estimated MR imaging parameter.

FIG. 4 shows an example of a display screen of the reference MR image and the estimated MR imaging parameter. A display screen D1 includes an MR image P1 assigned by the user to estimate a parameter and a table T1 that lists the estimated MR imaging parameters.

(Step SA4)

After the display screen D1 is displayed, the processing circuitry 51 presents a determination on whether or not there is a modification in the estimated MR imaging parameter to the user. Specifically, the processing circuitry 51 displays a GUI (not shown) on the display screen D1 so that the parameter can be modified, and performs the determination based on whether or not an input relating to a modification instruction made by the user has been received. In the case where a modification has not been made by the user, the processing proceeds to step SA6, and in the case where a modification has been made by the user, the processing proceeds to step SA5.

(Step SA5)

The processing circuitry 51 modifies the MR imaging parameter based on the modification instruction from the user. After step SA5, the processing proceeds to step SA6. Step SA3, step SA4, and step SA5 may be omitted.

(Step SA6)

After the processing relating to the modification of the MR imaging parameter, the processing circuitry 51 executes the output function 513. When the output function 513 is executed, the processing circuitry 51 outputs the MR imaging parameter to an MR imaging apparatus. It should be noted that the MR imaging apparatus is explained as being identical to the magnetic resonance imaging apparatus 1.

(Step SA7)

After receiving the MR imaging parameter, the processing circuitry 51 executes the imaging protocol setting function. When the imaging protocol setting function is executed, the processing circuitry 51 sets the imaging protocol based on the received MR imaging parameter, and outputs it to the sequence control circuitry 29. The sequence control circuitry 29 executes MR imaging and generates k-space data.

(Step SA8)

After the k-space data is generated, the processing circuitry 51 executes the image reconstruction function. When the image reconstruction function is executed, the processing circuitry 51 reconstructs the generated k-space data and generates MR image data.

(Step SA9)

After the MR image data is generated, the processing circuitry 51 executes the display control function 514. When the display control function 514 is executed, the processing circuitry 51 displays the MR image data (reference MR image) acquired in step SA1 and the generated MR image data (output MR image) on the display 53, and ends the MR imaging parameter estimation processing.

Figure 5:
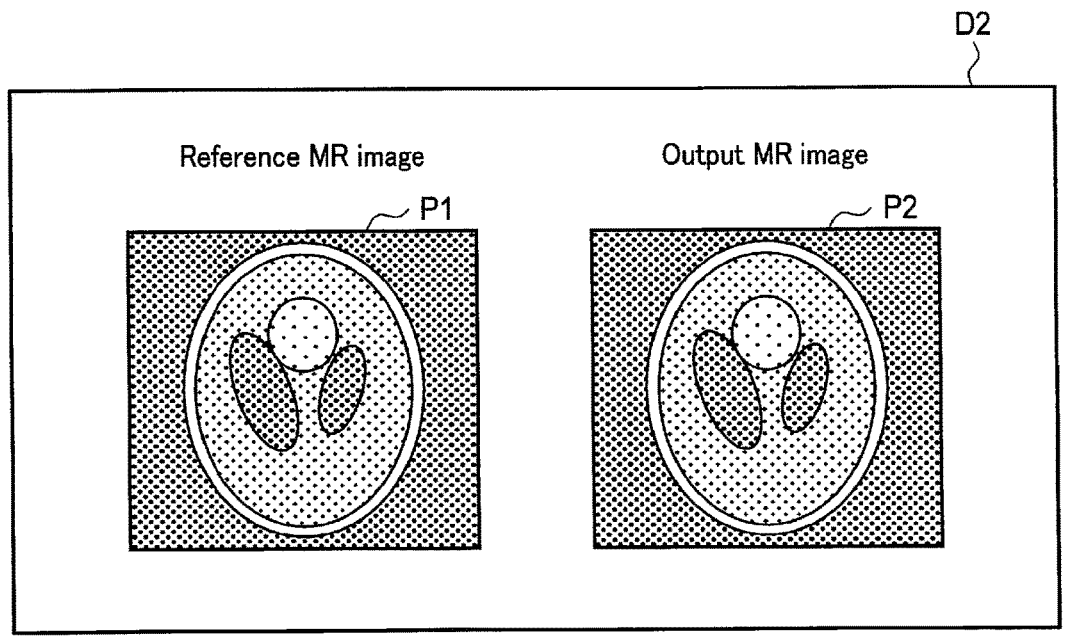
FIG. 5 shows an example of a display screen of a reference MR image and an output MR image.

FIG. 5 shows an example of a display screen of the reference MR image and the output MR image. A display screen D2 includes the MR image P1 and an MR image P2 obtained by the imaging based on the estimated MR imaging parameter.

In the flowchart of FIG. 3, the MR imaging parameter estimation processing is explained as including imaging processing; however, it is not limited thereto. In the case where the MR imaging parameter estimation processing does not include the imaging processing, the MR imaging parameter estimation processing includes at least step SA1, step SA2, and step SA6. Furthermore, the display of the MR imaging parameter in step SA2 may be omitted.

In the above, the medical image data input to the trained model has been explained as being the MR image data; however, it is not limited thereto. In the following FIG. 6 to FIG. 10, cases in which the medical image data to be input to the trained model is other than the MR image data will be explained. It should be noted that an output from the trained model is an MR imaging parameter in either of the cases. Furthermore, in FIG. 6 to FIG. 10, the MR imaging apparatus, which is an output destination of the MR imaging parameter, is omitted.

Figure 6:
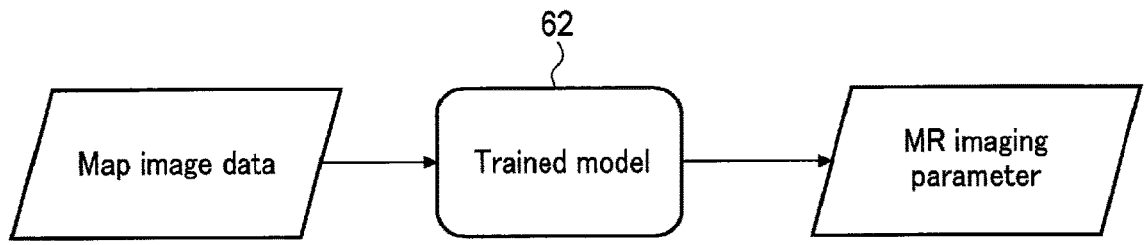
FIG. 6 shows a second example of input/output of a trained model used in the generating function of FIG. 1.

FIG. 6 shows a second example of input/output of the trained model used in the generating function of FIG. 1. By the generating function 512, the processing circuitry 51 applies a trained model 62 to map image data, and generates an MR imaging parameter relating to the map image data. A map image is, for example, an image (for example, a tumor-like map, a T1 map, a T2 map, and an ADC map) calculated from a plurality of MR images. In order to acquire the map image, it is necessary to perform imaging by a plurality of pulse sequences. Therefore, the trained model 62 is trained to output the MR imaging parameter corresponding to the number of pulse sequences. For example, in the case of the tumor-like map, the trained model 62 is trained to output a set of MR imaging parameters necessary for each of T1 weighting (T1W), T2 weighting (T2W), fluid-attenuated inversion recovery (FLAIR), and diffusion weighting (DWI).

Figure 7:
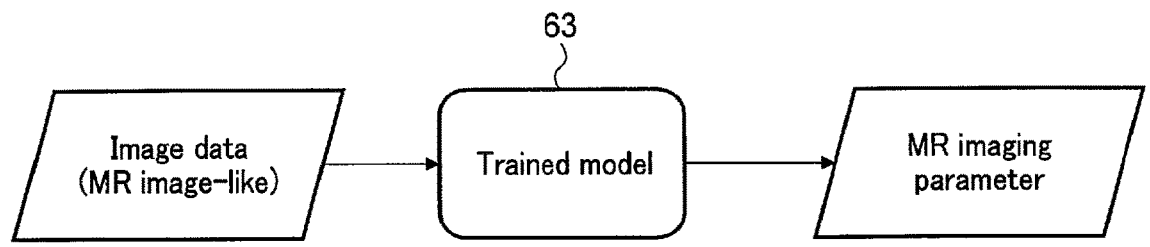
FIG. 7 shows a third example of input/output of a trained model used in the generating function of FIG. 1.

FIG. 7 shows a third example of input/output of the trained model used in the generating function of FIG. 1. By the generating function 512, the processing circuitry 51 applies a trained model 63 to MR image-like image data, and generates an MR imaging parameter relating to the MR image-like image data.

The above-mentioned trained model 60, trained model 62, and trained model 63 are explained as being trained, respectively, using a single type of input data; however, the trained models are not limited thereto. For example, the trained model may be trained using a plurality of types of input data.

Figure 8:
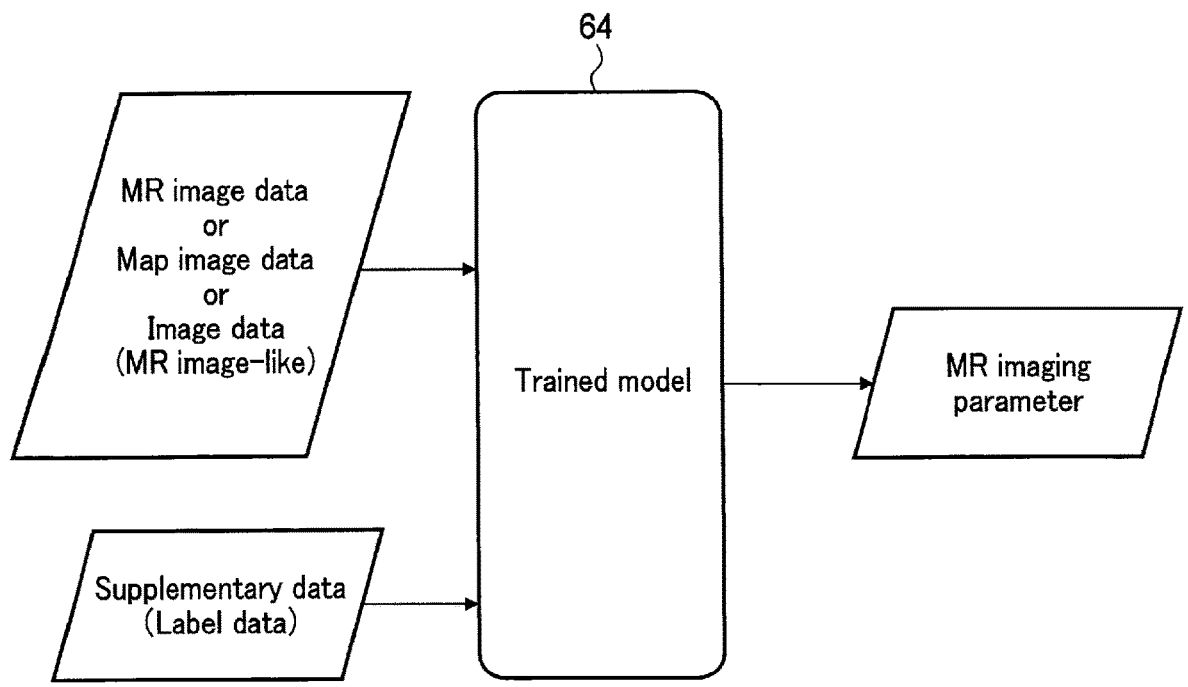
FIG. 8 shows a fourth example of input/output of a trained model used in the generating function of FIG. 1.

FIG. 8 shows a fourth example of input/output of the trained model used in the generating function of FIG. 1. By the generating function 512, the processing circuitry 51 applies a trained model 64 to the MR image data, the map image data, or the MR image-like image data, and supplementary data (label data) that specifies the type of the plurality of image data, and generates an MR imaging parameter relating to the specified image data. Specifically, the processing circuitry 51 switches among a plurality of models corresponding to the type of image data based on the label data. For example, the trained model 64 comprises the trained model 60, the trained model 62, and the trained model 63, respectively. Based on the label data, the processing circuitry 51 switches among the trained model 60, the trained model 62, and the trained model 63. It should be noted that, for example, these models may be divided into three independent models, or may have a weight switched per model by a software switch, etc. The label data described above can serve to function as, for example, the software switch.

The label data of FIG. 8 is data in which the type of input image data is digitized. For example, the label data may indicate a case where the MR image data is input as [1, 0, 0], a case where the map image data is input as [0, 1, 0], and a case where the MR image-like image data is input as [0, 0, 1]. That is, the label data associates a position of a value of a vector with the type of the image data, and expresses the presence of the type by the value of the vector.

Figure 9:
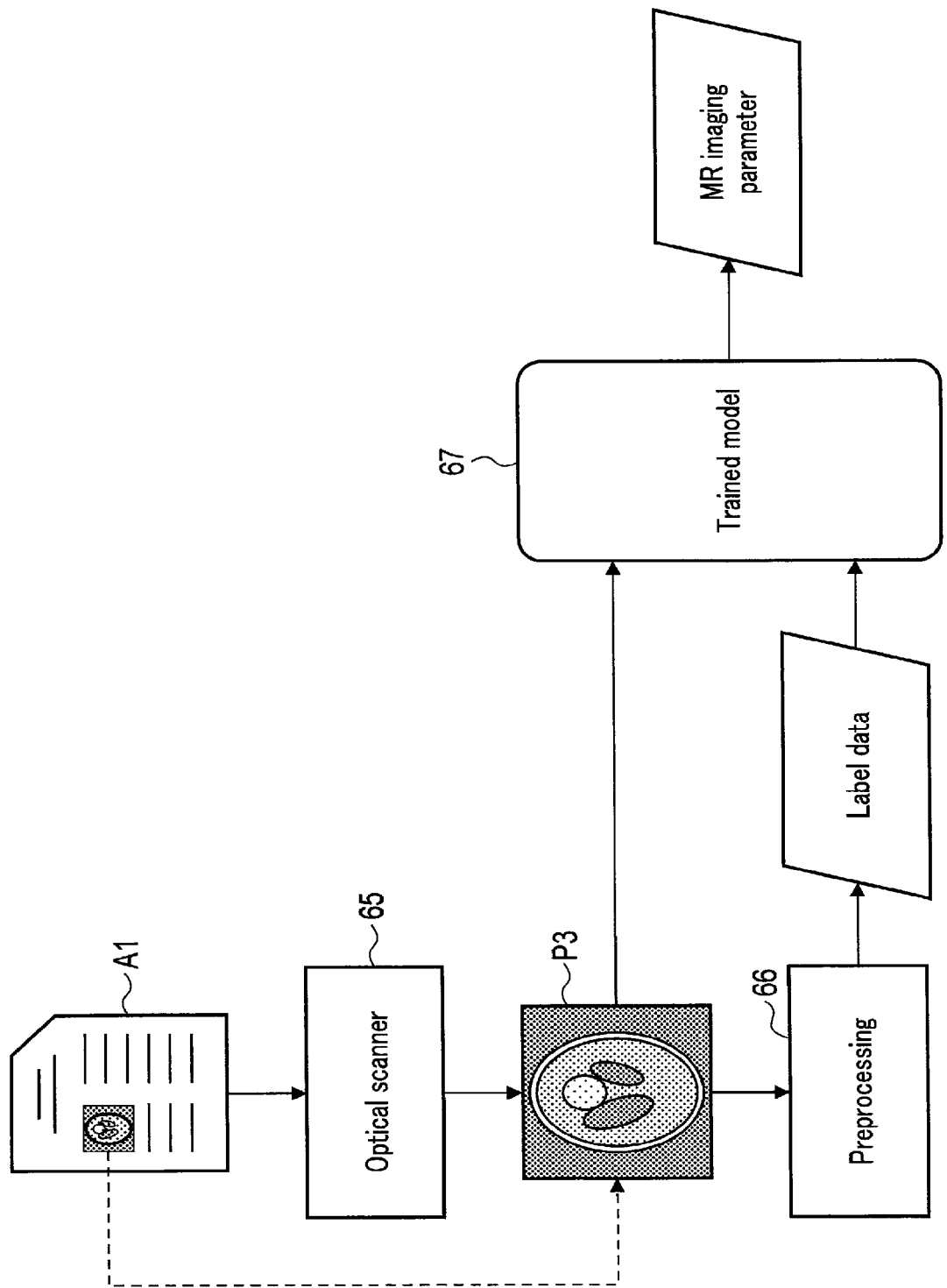
FIG. 9 shows a fifth example of input/output of a trained model used in the generating function of FIG. 1, and a specific example of processing relating to input.

FIG. 9 shows a fifth example of input/output of a trained model used in the generating function of FIG. 1, and a specific example of processing relating to input. In the example of FIG. 9, an MR imaging parameter of an MR image printed on an article A1 can be estimated. In the same manner as the trained model 64 of FIG. 8, a trained model 67 of FIG. 9 responds to input of a plurality of types of image data.

Specifically, the user reads the article A1 with an optical scanner 65, and acquires MR image-like image data P3. As preprocessing 66, the processing circuitry 51 generates label data from the acquired image data. P3. The label data here is the same as the label data of FIG. 8. By the generating function 512, the processing circuitry 51 applies the trained model 67 to the image data P3 and the label data, and generates an MR imaging parameter relating to the image data P3.

Figure 10:
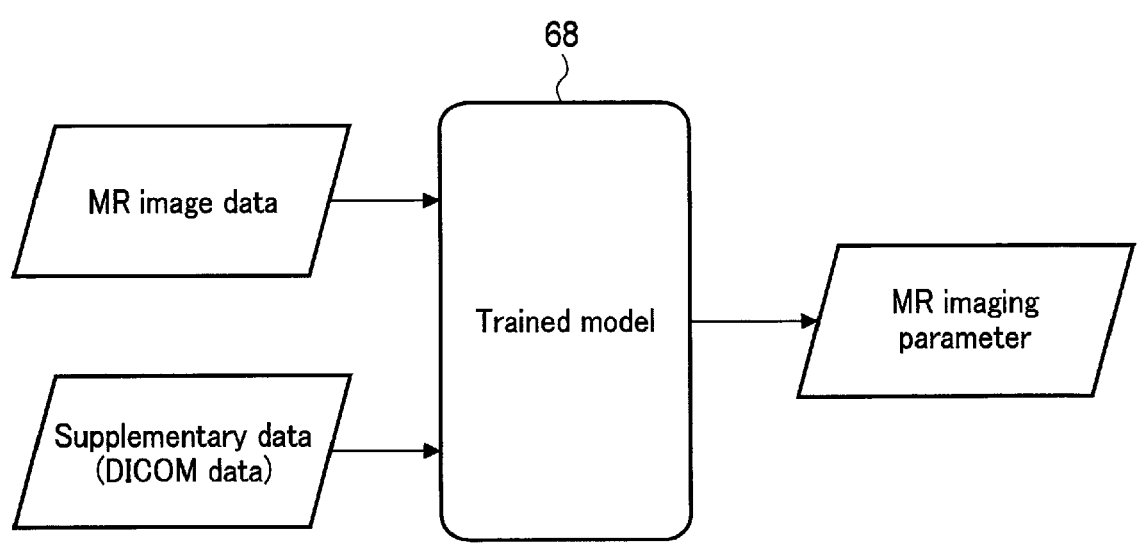
FIG. 10 shows a sixth example of input/output of a trained model used in the generating function of FIG. 1.

FIG. 10 shows a sixth example of input/output of a trained model used in the generating function of FIG. 1. By the acquisition function 511, the processing circuitry 51 acquires MR image data and supplementary data (DICOM data) relating to the MR image data. By the generating function 512, the processing circuitry 51 applies a trained model 68 to the MR image data and the DICOM data relating to the MR image data, and generates an MR imaging parameter relating to the MR image data. In the case where there is a difference between the input DICOM data and the generated MR imaging parameter, when outputting the MR imaging parameter to a subsequent MR imaging apparatus, the processing circuitry 51 may change the value of the known DICOM data to the value of the MR imaging parameter.

Preferably, the type of DICOM tag to be included in the DICOM data of FIG. 10 is predetermined at a design stage. Accordingly, when inputting the DICOM data to the trained model 68, the processing circuitry 51 may attach label data in a one-hot vector format indicating the presence of the DICOM tag included in the DICOM data to the DICOM data.

As explained above, the magnetic resonance imaging apparatus according to the first embodiment acquires MR image data, and generates an MR imaging parameter by inputting the MR image data to a trained model, the MR imaging parameter being a parameter of the magnetic resonance imaging apparatus with respect to the MR image data, the trained model being trained to generate an MR imaging parameter of the magnetic resonance imaging apparatus based on an MR image data. Therefore, the magnetic resonance imaging apparatus according to the present embodiment is capable of estimating an MR imaging parameter used for MR imaging from MR image data of which the MR imaging parameter is unknown so that, for example, a user may set an optimal MR imaging parameter.

Second Embodiment

In the first embodiment, the medical data processing apparatus is explained as being a computer mounted on the magnetic resonance imaging apparatus. On the other hand, in the second embodiment, the medical data processing apparatus will be explained as being a computer mounted on an X-ray computed tomography apparatus. In the following explanation, constituent elements having functions almost identical to those in the first embodiment will be given identical symbols, and will be provided with explanations only when necessary.

Figure 11:
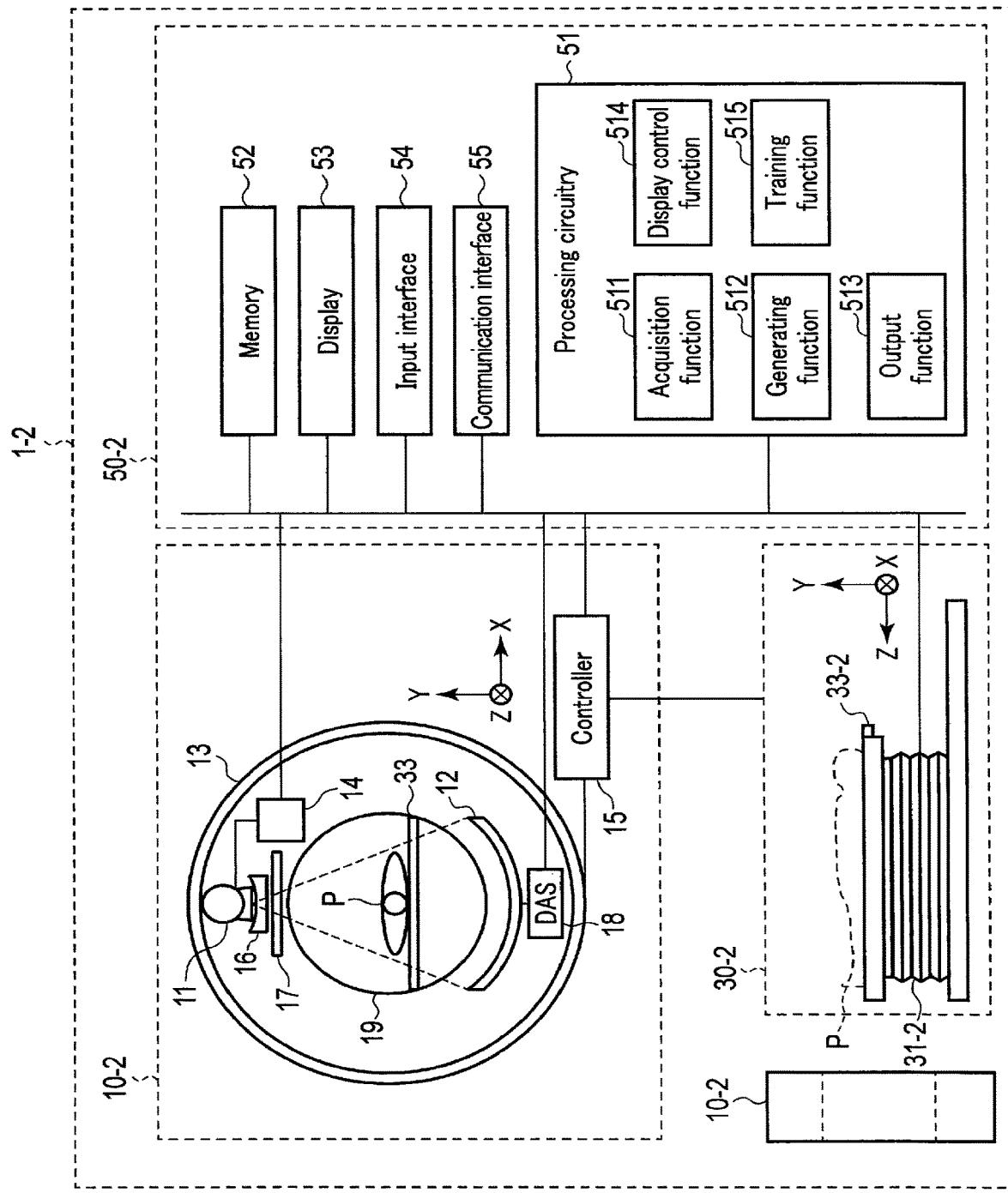
FIG. 11 shows a configuration of an X-ray computed tomography apparatus according to a second embodiment.

FIG. 11 shows a configuration of an X-ray computed tomography apparatus according to the second embodiment. In FIG. 11, a plurality of gantries 10-2 are illustrated for convenience of explanation; however, typically, the X-ray computed tomography apparatus is equipped with one gantry 10-2.

As shown in FIG. 11, the X-ray computed tomography apparatus 1-2 includes a gantry 10-2, a couch 30-2, and a medical data processing apparatus (console) 50-2. The gantry 10-2 is a scanning apparatus having a configuration for performing X-ray CT imaging on a subject P. The couch 30-2 is a carrier device on which the subject P to be the X-ray CT imaging target is placed, and is for positioning the subject P. The medical data processing apparatus 50-2 is a computer for controlling the gantry 10-2. For example, the gantry 10-2 and the couch 30-2 are installed in an examination room, and the medical data processing apparatus 50-2 is installed in a control room adjacent to the examination room. The gantry 10-2, the couch 30-2, and the medical data processing apparatus 50-2 are connected by cable or wirelessly in a communicable manner with each other.

As shown in FIG. 11, the gantry 10-2 includes an X-ray tube 11, an X-ray detector 12, a rotation frame 13, an X-ray high-voltage apparatus 14, a controller 15, a wedge filter 16, a collimator 17, and a data acquisition system (DAS) 18.

The X-ray tube 11 generates an X-ray. Specifically, the X-ray tube 11 includes a negative electrode for generating thermoelectrons, a positive electrode for generating X-rays by receiving the thermoelectrons flying from the negative electrode, and a vacuum tube for maintaining the negative electrode and the positive electrode. The X-ray tube 11 is connected to the X-ray high-voltage apparatus 14 via a high-voltage cable. A filament current is supplied to the negative electrode by the X-ray high-voltage apparatus 14. By supplying the filament current, the thermoelectrons are generated from the negative electrode. A tube voltage is applied between the negative electrode and the positive electrode by the X-ray high-voltage apparatus 14. By applying the tube voltage, thermoelectrons fly toward the positive electrode from the negative electrode and collide with the positive electrode, thereby generating an X-ray. The generated X-ray is irradiated on the subject P. The thermoelectrons flying from the negative electrode to the positive electrode causes a tube current to flow.

The X-ray detector 12 detects the X-ray generated from the X-ray tube 11 passing through the subject P, and outputs an electric signal corresponding to the detected X-ray dose to the DAS 18. The X-ray detector 12 has a structure in which a plurality of X-ray detecting element rows, in each row of which a plurality of X-ray detecting elements are arranged in a channel direction, are arranged in a slice direction (a row direction). The X-ray detector 12 is, for example, an indirect conversion-type detector having a grid, a scintillator array, and a photosensor array. The scintillator array has a plurality of scintillators. Scintillators output light of a light quantity in accordance with an incident X-ray dose. The grid has an X-ray shielding plate that is arranged on an X-ray incident surface side of the scintillator array and absorbs scattered X-rays. The grid may be referred to as a collimator (a one-dimensional collimator or a two-dimensional collimator). The photosensor array converts the light from the scintillator into an electric signal in accordance with the light quantity thereof. As a photosensor, for example, a photodiode is used.

The rotation frame 13 is an annular frame for supporting the X-ray tube 11 and the X-ray detector 12 rotatably about a rotational axis Z. Specifically, the rotation frame 13 supports the X-ray tube 11 and the X-ray detector 12 opposite each other. The rotation frame 13 is rotatably supported about the rotational axis Z by a fixed frame (not shown). When the rotation frame 13 is rotated about the rotational axis Z by the controller 15, the X-ray tube 11 and the X-ray detector 12 are rotated about the rotational axis Z. A field of view (FOV) is set in an opening 19 of the rotation frame 13.

In the present embodiment, a rotational axis of the rotation frame 13 in a non-tilting state or a longitudinal direction of a table top 33-2 of the couch 30-2 is defined as a Z direction, a direction orthogonal to the Z direction and horizontal to a floor surface is defined as an X direction, and a direction orthogonal to the Z direction and perpendicular to the floor surface is defined as a Y direction.

The X-ray high voltage apparatus 14 includes a high-voltage generator and an X-ray controller. The high-voltage generator includes electrical circuitry such as a transformer (trans) and a rectifier, and generates a high voltage to be applied to the X-ray tube 11 and a filament current to be supplied to the X-ray tube 11. The X-ray controller controls the high-voltage to be applied to the X-ray tube 11 and the filament current to be supplied to the X-ray tube 11. The high-voltage generator may be a transformer type or may be an inverter type. The X-ray high-voltage apparatus 14 may be provided on the rotation frame 13 inside the gantry 10-2, or may be provided on a fixed frame (not shown) inside the gantry 10-2.

The wedge filter 16 adjusts the dose of X-ray to be irradiated on the subject P. Specifically, the wedge filter 16 attenuates the X-ray so that the X-ray dose to be irradiated on the subject P from the X-ray tube 11 has a predetermined distribution. For example, as the wedge filter 16, a metal filter formed by processing metal such as aluminum is used. The wedge filter 16 is processed to have a predetermined target angle or a predetermined thickness. The wedge filter 16 is also referred to as a bow-tie filter.

The collimator 17 limits an irradiation range of the X-ray passing through the wedge filter 16. The collimator 17 slidably supports a plurality of lead plates shielding the X-ray, and adjusts the shape of slit formed by the plurality of lead plates. The collimator 17 is also referred to as an X-ray diaphragm.

The DAS 18 reads an electric signal in accordance with the X-ray dose detected by the X-ray detector 12 from the X-ray detector 12, amplifies the read electric signal, and integrates the electric signal over a view period to acquire projection data having a digital value in accordance with the X-ray dose over the view period. The DAS 18 is realized by, for example, ASIC which is equipped with a circuit element that is capable of generating projection data. The projection data generated by the DAS 18 is transmitted from a transmitter having a light-emitting diode (LED) provided on the rotation frame 13 to a receiver having a light-emitting diode (LED) provided on a non-rotating portion (for example, a fixed frame) of the gantry 10-2 by optical communication, and is transmitted from the receiver to the medical data processing apparatus 50-2. The transmission method of the projection data from the rotation frame 13 to the non-rotating portion of the gantry 10-2 is not limited to the aforementioned optical communication, and may be any method as long as it is a non-contact type data transmission.

The couch 30-2 comprises a base 31-2 and the table top 33-2. The base 31-2 is installed on a floor surface. The base 31-2 has a structure that supports a support frame movably in a direction (Y direction) perpendicular to the floor surface. The support frame is a frame provided on an upper part of the base 31-2. The support frame supports the table top 33-2 slidably along a center axis Z. The table top 33-2 has a flexible plate-like structure on which the subject P is placed. A couch motor is accommodated in the couch 30-2. The couch motor is a motor or an actuator that generates power for moving the table top 33-2 on which the subject P is placed. The couch motor operates under the control of the controller 15 or the medical data processing apparatus 50-2, etc.

The controller 15 controls the X-ray high voltage apparatus 14, the DAS 18, and the couch 30-2 in order to execute X-ray CT imaging in accordance with an imaging control performed by processing circuitry 51. The controller 15 includes processing circuitry including a CPU, etc., and a drive apparatus, such as a motor and an actuator. The processing circuitry includes a processor, such as a CPU, and a memory, such as ROM and RAM, as hardware resources. The controller 15 controls the gantry 10-2 and the couch 30-2 in accordance with, for example, a control signal received from an input interface 54 provided on the medical data processing apparatus 50-2, the gantry 10-2, and the couch 30-2, etc. For example, the controller 15 controls rotation of the rotation frame 13, tilt of the gantry 10-2, and operations of the table top 33-2 and the couch 30-2.

The medical data processing apparatus 50-2 shown in FIG. 11 is a computer including the processing circuitry 51, a memory 52, a display 53, the input interface 54, and a communication interface 55.

The processing circuitry 51 is, for example, a processor that functions as a core of the X-ray computed tomography apparatus 1-2. The processing circuitry 51 executes a program stored in the memory 52 to realize a function corresponding to the program. The processing circuitry 51 realizes, for example, an acquisition function 511, a generating function 512, an output function 513, a display control function 514, and a training function 515. Although not shown, the processing circuitry 51 realizes an imaging control function, a reconfiguration processing function, an image processing function, a similarity calculation function, and a weight changing function.

In the imaging control function, the processing circuitry 51 controls the X-ray high voltage apparatus 14, the controller 15, and the DAS 18 to perform CT imaging. The processing circuitry 51 controls the X-ray high voltage apparatus 14, the controller 15, and the DAS 18 in accordance with a user instruction via the input interface 54, or an automatically set photographing condition (CT imaging parameter). The CT imaging parameter will be described later.

In the reconstruction processing function, the processing circuitry 51 generates a CT image based on the projection data output from the DAS 18. Specifically, the processing circuitry 51 performs preprocessing such as logarithmic conversion processing or offset correction processing, sensitivity correction processing between channels, and beam hardening correction with respect to the projection data output from the DAS 18. The processing circuitry 51 then performs reconstruction processing with respect to the preprocessed projection data using a filter correction back projection method or an iterative approximation reconstruction method, etc., and generates the CT image.

In the image processing function, the processing circuitry 51 converts the CT image generated by the reconstruction processing function into a tomogram of an arbitrary cross section or a three-dimensional image based on an input operation received from an operator via the input interface 54.

Explanations on the memory 52, the display 53, the input interface 54, the communication interface 55, the acquisition function 511, the generating function 512, the output function 513, the display control function 514, and the training function 515 will be omitted. Furthermore, the similarity calculation function and the weight changing function will be described later.

Hereinafter, an operation example of the X-ray computed tomography apparatus 1-2 according to the present embodiment will be explained.

Figure 12:
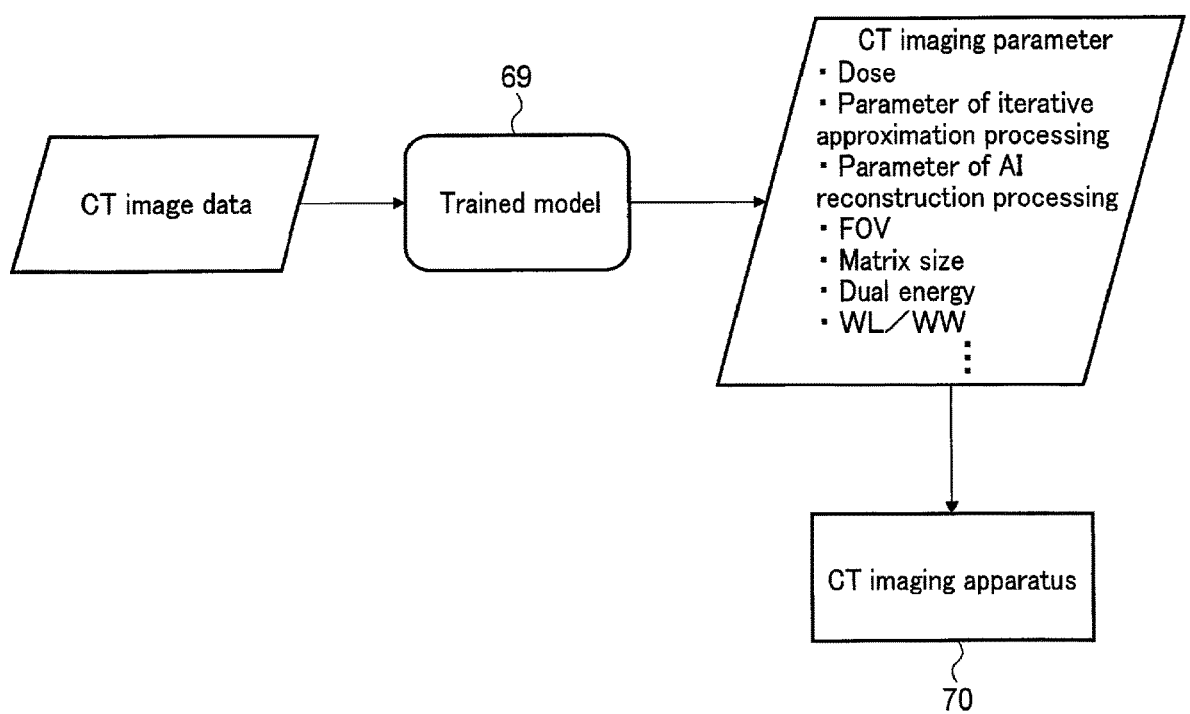
FIG. 12 shows a first example of input/output of a trained model used in a generating function of FIG. 11, and a CT imaging apparatus of an output destination.

FIG. 12 shows a first example of input/output of a trained model used in the generating function of FIG. 11, and a CT imaging apparatus of an output destination. By the acquisition function 511, the processing circuitry 51 acquires CT image data. By the generating function 512, the processing circuitry 51 applies a trained model 69 to the CT image data and generates a CT imaging parameter relating to the CT image data. By the output function 513, the processing circuitry 51 outputs the CT imaging parameter to a CT imaging apparatus 70.

The CT imaging parameter is a parameter relating to imaging of an X-ray computed tomography apparatus when acquiring the CT image data. Furthermore, the CT imaging parameter may include information relating to the X-ray computed tomography apparatus.

Examples of the CT imaging parameter include a dose, a parameter of iterative approximation processing, a parameter of AI reconstruction processing, FOV, a matrix size, dual energy, window level/window width (WL/WW), types of acquisition bins, or information on the number of rows of multi-slices.

The dose includes, for example, information on the value of the tube current and information on the value of the tube voltage. The parameter of iterative approximation processing includes, for example, information on the type of iterative approximation processing (for example, an expectation maximization (EM) method and an algebraic reconstruction technique (ART) method) and information on a blend rate. The blend rate indicates a composition ratio between an initial image and an updated image used in the iterative approximation processing. The parameter of AI reconstruction processing includes, for example, information relating to a noise reduction rate. The dual energy includes, for example, information on whether or not dual energy is used.

Figure 13:
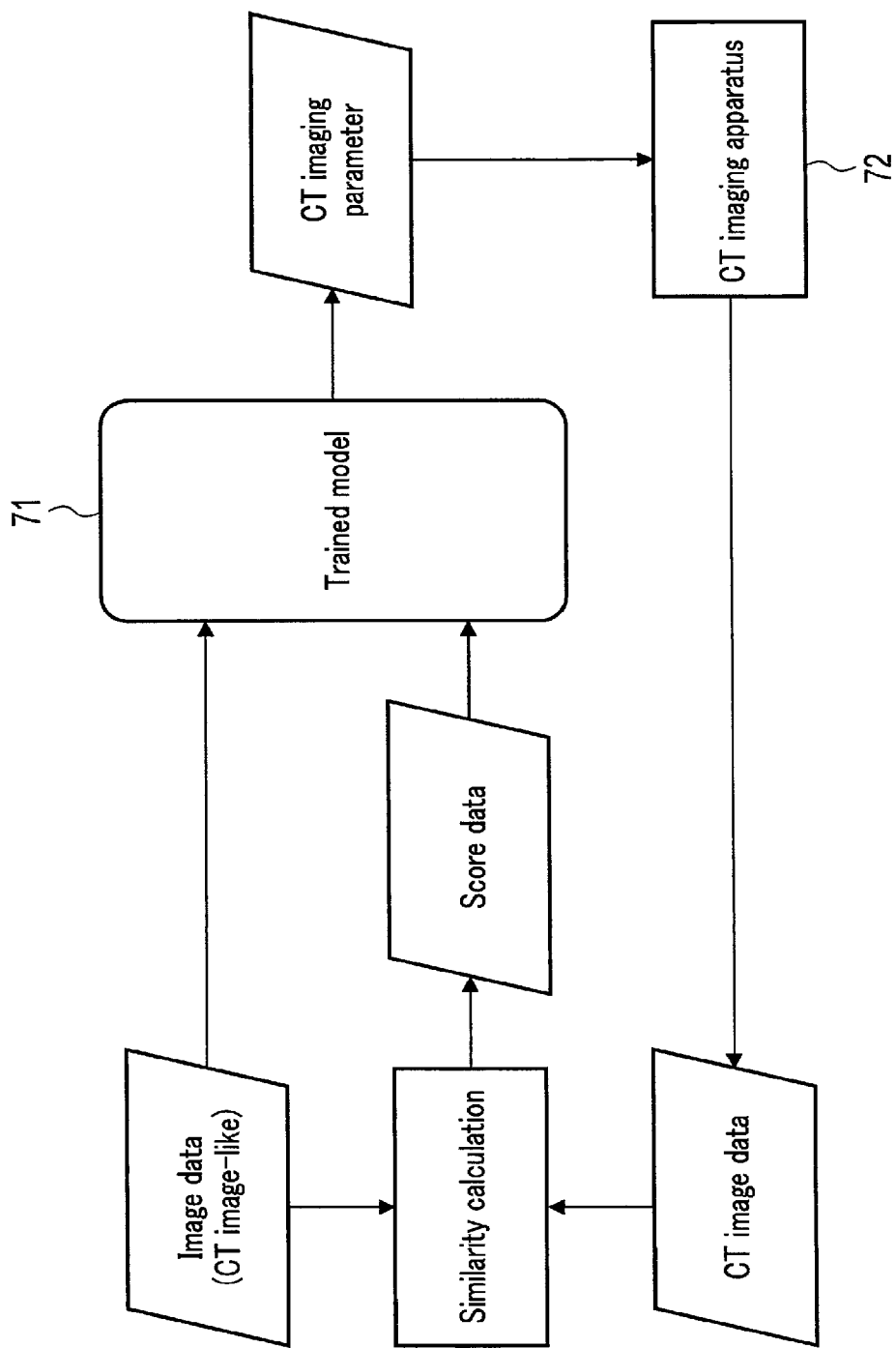
FIG. 13 shows a second example of input/output of a trained model used in a generating function of FIG. 12, a CT imaging apparatus of an output destination, and a specific example of processing relating to input.

FIG. 13 shows a second example of input/output of a trained model used in the generating function of FIG. 12, a CT imaging apparatus of an output destination, and a specific example of processing relating to input. In the example of FIG. 13, display of a CT image generated in real time can be optimized by generating a CT imaging parameter based on CT image-like image data to be of reference, executing imaging based on the generated CT image parameter, and feeding back information on CT image data generated by the imaging to the generating processing of the CT imaging parameter. Summarizing FIG. 13, the X-ray computed tomography apparatus 1-2 is capable of performing feedback control in real time for the display of the CT image by using the CT image data generated by the CT imaging.

It should be noted that, in FIG. 13, although the CT image-like image data is input to a trained model 71, the data is not limited thereto, and may be the CT image data. Furthermore, the trained model 71 of FIG. 13 is capable of changing the weight of the model based on score data, and varying each value of the CT imaging parameter.

Figure 14:
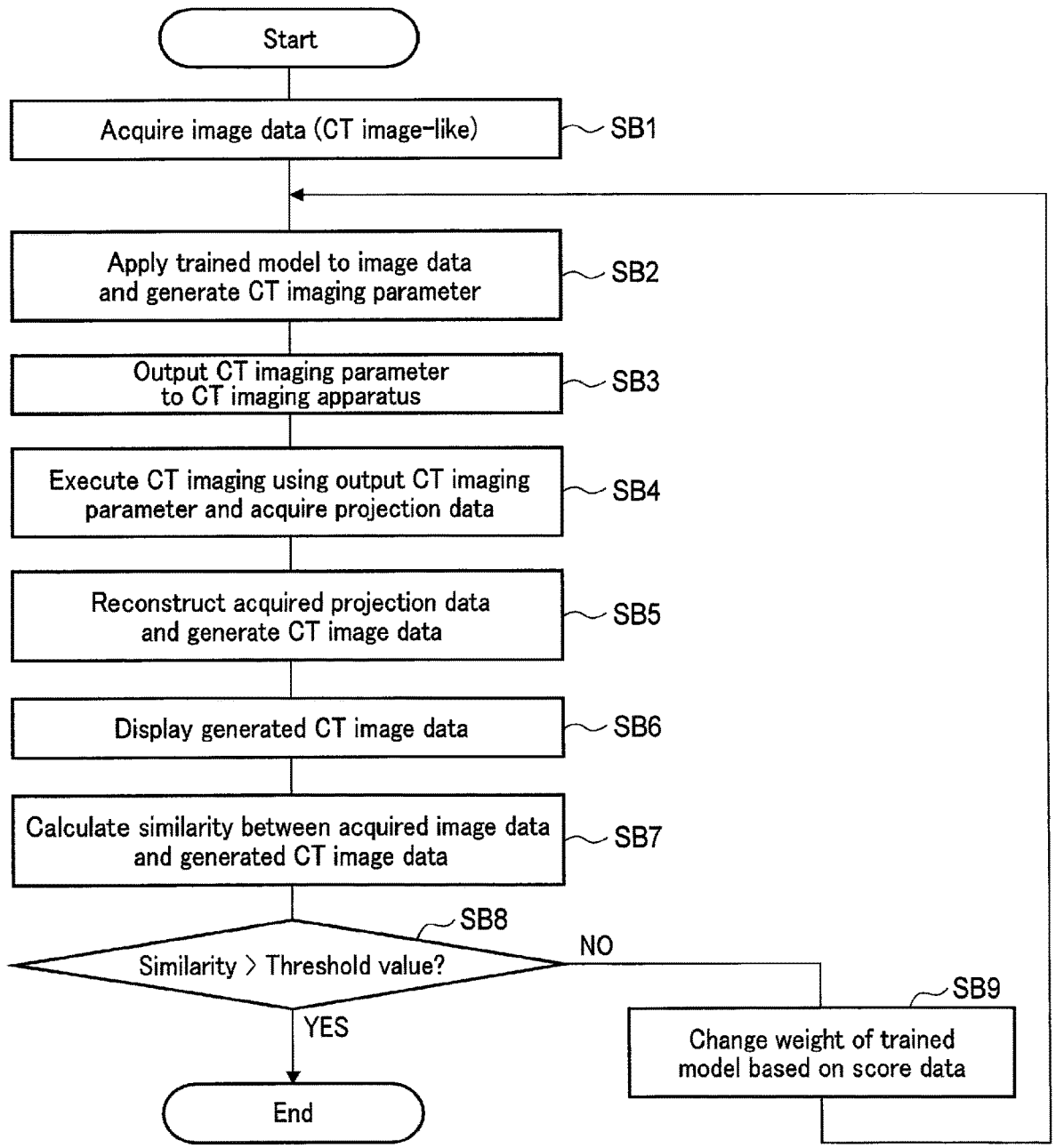
FIG. 14 is a flowchart for explaining a series of events including CT imaging parameter estimation processing in the second embodiment relating to FIG. 13.

FIG. 14 is a flowchart for explaining a series of events including CT imaging parameter estimation processing in the second embodiment relating to FIG. 13. For example, the flowchart of FIG. 14 starts by the processing circuitry 51 executing a CT imaging parameter estimation program, which is triggered by an instruction to activate an application relating to the CT imaging parameter estimation processing input by a user.

(Step SB1)

When the CT imaging parameter estimation program is executed, the processing circuitry 51 executes the acquisition function 511. When the acquisition function 511 is executed, the processing circuitry 51 acquires CT image-like image data assigned by the user.

(Step SB2)

After acquiring the CT image-like image data, the processing circuitry 51 executes the generating function 512. When the generating function 512 is executed, the processing circuitry 51 applies the trained model 71 to the CT image-like image data and generates a CT imaging parameter relating to the CT image-like image data.

(Step SB3)

After generating the CT imaging parameter, the processing circuitry 51 executes the output function 513. When the output function 513 is executed, the processing circuitry 51 outputs the CT imaging parameter to a CT imaging apparatus 72. The CT imaging apparatus 72 will be explained as being identical to the X-ray computed tomography apparatus 1-2.

(Step SB4)

After receiving the CT imaging parameter, the processing circuitry 51 executes the imaging control function. When the imaging control function is executed, the processing circuitry 51 executes CT imaging using the CT imaging parameter generated in step SB2, and acquires projection data.

(Step SB5)

After acquiring the projection data, the processing circuitry 51 executes the reconstruction processing function. When the reconstruction processing function is executed, the processing circuitry 51 reconstructs the acquired projection data and generates CT image data.

(Step SB6)

After generating the CT image data, the processing circuitry 51 executes the display control function 514. When the display control function 514 is executed, the processing circuitry 51 displays the generated CT image data on the display 53.

(Step SB7)

After the CT image data is displayed, the processing circuitry 51 executes the similarity calculation function. When the similarity calculation function is executed, the processing circuitry 51 calculates the similarity between the CT image-like image data acquired in step SB1 and the generated CT image data. For example, the similarity is obtained based on a feature amount that is calculated for each image data.

(Step SB8)

After the similarity is calculated, the processing circuitry 51 determines whether or not the calculated similarity is higher than a threshold value. In the case where the similarity is higher than the threshold value, it is determined that the display of the CT image generated in real time is optimized, and the processing is ended. In the case where the similarity is equal to or lower than the threshold value, it is determined that the display of the CT image generated in real time is not optimized, and the processing proceeds to step SB9.

(Step SB9)

After performing the processing relating to the determination of the similarity, the processing circuitry 51 executes the weight changing function. When the weight changing function is executed, the processing circuitry 51 changes the weight of the trained model 71 based on score data corresponding to the similarity. After step SB9, the processing returns to step SB2.

In the flowchart of FIG. 14, an example of optimizing the display of the CT image generated in real time has been explained; however, this is not limited to real time. For example, the CT imaging may be executed only by the initially estimated CT imaging parameter, and the CT imaging parameter estimated after the second estimation may be used for optimizing the display screen of the generated CT image. Specifically, the processing circuitry 51 optimizes the display screen of the CT image data by using WL/WW included in the CT imaging parameter estimated after the second estimation.

As explained above, the X-ray computed tomography apparatus according to the second embodiment acquires CT image data, and generates a CT imaging parameter by inputting the CT image data to a trained model, the CT imaging parameter being a parameter of the X-ray computed tomography apparatus with respect to the CT image data, the trained model being trained to generate a CT imaging parameter of the X-ray computed tomography apparatus based on a CT image data. Therefore, the X-ray computed tomography apparatus according to the present embodiment is capable of estimating a CT imaging parameter used for CT imaging from CT image data of which the CT imaging parameter is unknown so that, for example, a user may set an optimal CT imaging parameter.

Third Embodiment

In the second embodiment, the medical data processing apparatus is explained as being a computer mounted on the X-ray computed tomography apparatus. On the other hand, in the third embodiment, the medical data processing apparatus will be explained as being a computer mounted on an ultrasound diagnostic apparatus. In the following explanation, constituent elements having functions almost identical to those in the first embodiment will be given identical symbols, and will be provided with explanations only when necessary.

Figure 15:
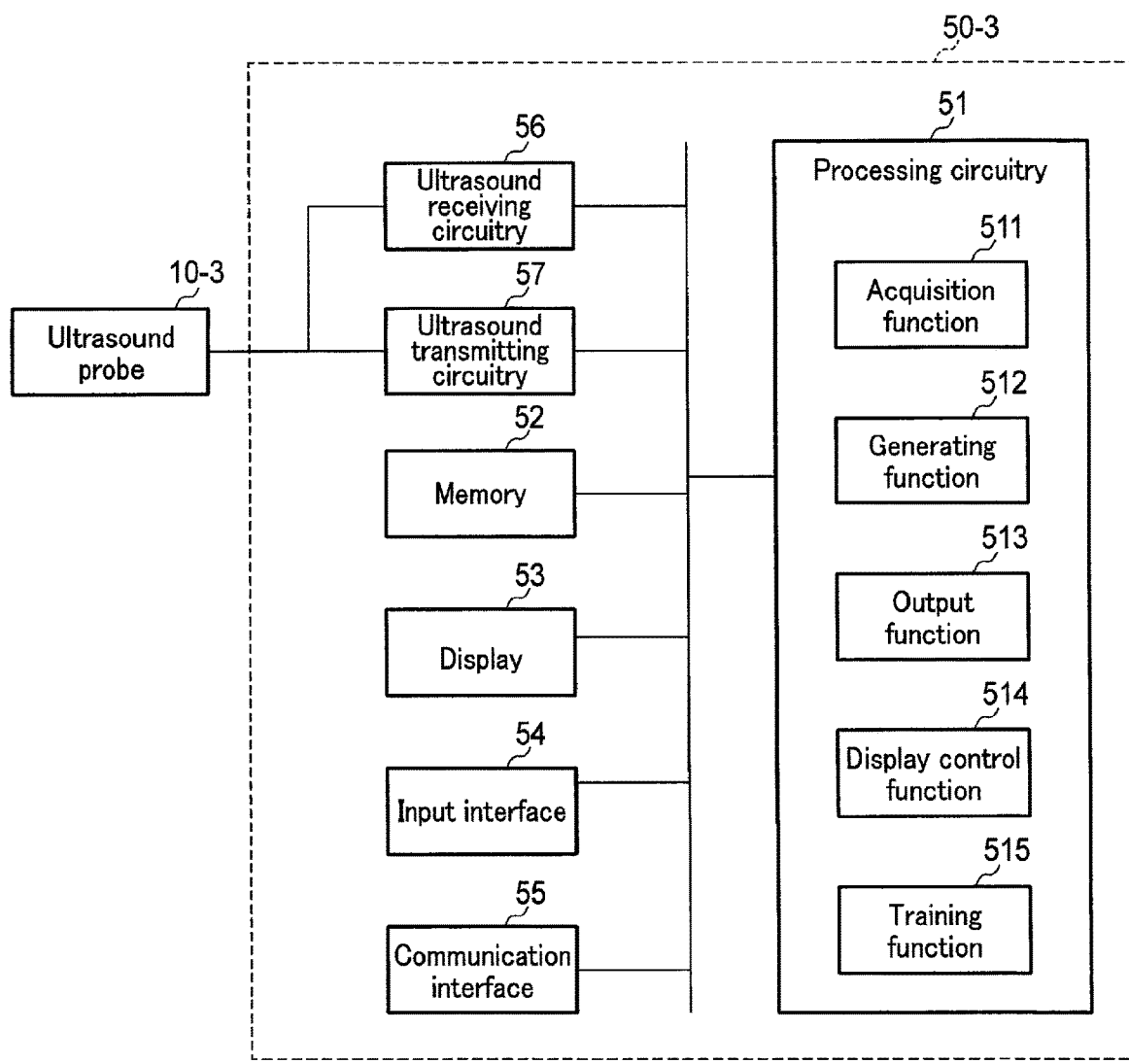
FIG. 15 shows a configuration of an ultrasound diagnostic apparatus according to a third embodiment.

FIG. 15 shows a configuration of the ultrasound diagnostic apparatus according to the third embodiment. As shown in FIG. 15, an ultrasound diagnostic apparatus 1-3 includes an ultrasound probe 10-3 and a medical data processing apparatus (apparatus main body) 50-3.

For example, the ultrasound probe 10-3 executes ultrasound scanning for a scanning region inside a living body of a patient, etc. in accordance with a control of the medical data processing apparatus 50-3. The ultrasound probe 10-3 includes, for example, a plurality of piezoelectric vibrators, a matching layer, and a backing material. In the present embodiment, the ultrasound probe 10-3 includes, for example, a plurality of piezoelectric vibrators arranged along a predetermined direction. The ultrasound probe 10-3 is detachably connected to the medical data processing apparatus 50-3.

The plurality of piezoelectric vibrators generate ultrasound in accordance with a drive signal supplied from ultrasound transmitting circuitry 57 included in the medical data processing apparatus 50-3. This allows the ultrasound probe 10-3 to transmit ultrasound to the living body. When the ultrasound is transmitted to the living body from the ultrasound probe 10-3, the transmitted ultrasound waves are continuously reflected on a discontinuous surface having an acoustic impedance in a tissue of the living body, and is received by a plurality of piezoelectric vibrators as a reflected wave signal. An amplitude of the received reflected wave signal depends on an acoustic impedance difference at the discontinuous surface on which the ultrasound is reflected. Furthermore, a reflected wave signal obtained in the case where a transmitted ultrasound pulse is reflected on a moving bloodstream or a surface of a radiation-absorbency tissue spacer, etc. depends on a velocity component in an ultrasound transmission direction of a moving body and is frequency shifted due to the Doppler effect. The ultrasound probe 10-3 receives the reflected wave signal from the living body and converts it into an electric signal. The electric signal is supplied to the medical data processing apparatus 50-3.

The medical data processing apparatus 50-3 show in FIG. 15 is a computer for generating and displaying an ultrasound image based on the reflected wave signal received by the ultrasound probe 10-3. As shown in FIG. 15, the medical data processing apparatus 50-3 includes the ultrasound transmitting circuitry 57, ultrasound receiving circuitry 56, processing circuitry 51, a memory 52, a display 53, an input interface 54, and a communication interface 55.

The ultrasound transmitting circuitry 57 is a processor for supplying a drive signal to the ultrasound probe 10-3. The ultrasound transmitting circuitry 57 is executed by, for example, trigger generating circuitry, delay circuitry, and pulsar circuitry. The trigger generating circuitry repeatedly generates a rate pulse for forming transmission ultrasound by a predetermined rate frequency. The delay circuitry provides each rate pulse generated by the trigger generating circuitry with a delay time for each piezoelectric vibrator necessary for converging the ultrasound generated by the ultrasound probe 10-3 into a beam and determining transmission directivity. At a timing based on the rate pulse, the pulsar circuitry applies the drive signal (drive pulse) to a plurality of ultrasound vibrators provided on the ultrasound probe 10-3. By arbitrarily varying the delay time to be provided to each rate pulse by the delay circuitry, a transmission direction from a piezoelectric vibrator surface is arbitrarily adjusted.

The ultrasound receiving circuitry 56 is a processor that performs various types of processing with respect to the reflected wave signal received by the ultrasound probe 10-3 and generates a reception signal. The ultrasound receiving circuitry 56 is realized by, for example, amplifier circuitry, an A/D converter, reception delay circuitry, and an adder. The amplifier circuitry amplifies the reflected wave signal received by the ultrasound probe 10-3 for each channel, and performs gain correction processing. The A/D converter converts the reflected wave signal to which gain correction is applied into a digital signal. The reception delay circuitry provides the digital signal with a delay time necessary for determining reception directivity. The adder adds a plurality of digital signals to which the delay time is given. By the adding processing performed by the adder, a reception signal in which a reflection component is emphasized from a direction in accordance with the reception directivity is generated.

The processing circuitry 51 is a processor that functions, for example, as a core of the ultrasound diagnostic apparatus 1-3. The processor circuitry 51 executes a program stored in the memory 52 to realize a function corresponding to the program. The processing circuitry 51 includes, for example, an acquisition function 511, a generating function 512, an output function 513, a display control function 514, and a training function 515. Although not shown, it should be noted that the processing circuitry 51 includes a B-mode processing function, a Doppler mode processing function, an image processing function, a similarity calculation function, and a weight changing function.

In the B-mode processing function, the processing circuitry 51 generates B-mode data based on the reception signal received from the ultrasound receiving circuitry 56. Specifically, for example, the processing circuitry 51 performs envelope detection processing and logarithmic amplification processing, etc. on the reception signal received from the ultrasound receiving circuitry 56, and generates data (B-mode data) in which signal strength is expressed by the brightness of luminance. The generated B-mode data is stored in a RAW data memory (not shown) as data on a two-dimensional ultrasound scanning line (raster).

In the Doppler-mode processing function, the processing circuitry 51 performs frequency analysis on the reception signal received from the ultrasound receiving circuitry 56 to generate data (Doppler data) in which motion information based on the Doppler effect of a bloodstream in a region of interest (ROI) set in a scan region is extracted. Specifically, the processing circuitry 51 generates Doppler data in which an average velocity, an average dispersion value, and average power, etc. at each of a plurality of sample points are estimated as the motion information of the bloodstream. The generated Doppler data is stored in the RAW data memory (not shown) as data on the two-dimensional ultrasound scanning line.

Furthermore, in the Doppler mode processing function, the processing circuitry 51 is capable of executing a color Doppler method which is referred to as a color flow mapping (CFM) method. In the CFM method, ultrasound transmission/reception is performed a number of times on a plurality of scanning lines. By applying a moving target indicator (MTI) filter with respect to data rows of the same position, the processing circuitry. 51 suppresses a signal (clutter signal) derived from a stationary tissue or a slow moving tissue, and extracts a signal derived from a bloodstream. The processing circuitry 51 then estimates information on the velocity, the dispersion, or the power, etc. of the bloodstream from the extracted signal.

In the image processing function, the processing circuitry 51 generates various types of ultrasound image data based on data generated by the B-mode processing function and the Doppler processing function. Specifically, the processing circuitry 51 generates B-mode image data configured by pixels by executing, for example, a RAW-pixel conversion with respect to B-mode RAW data stored in the RAW data memory, which is, for example, executing coordinate conversion in accordance with an ultrasound scanning mode by the ultrasound probe 10-3.

Furthermore, in the image processing function, the processing circuitry 51 executes, for example, image processing, such as RAW-pixel conversion, with respect to Doppler RAW data stored in the RAW data memory to generate Doppler image data in which bloodstream information is visualized. The Doppler image data is velocity image data, dispersion image data, power image data, or image data obtained by combinations thereof. It should be noted that the Doppler image data generated from Doppler data acquired by the color Doppler method may be referred to as color Doppler ultrasound image data.

The explanations on the memory 52, the display 53, the input interface 54, the communication interface 55, the acquisition function 511, the generating function 512, the output function 513, the display control function 514, and the training function 515 will be omitted. Furthermore, the similarity calculation function and the weight changing function will be described later.

Hereinafter, the ultrasound diagnostic apparatus 1-3 according to the present embodiment will be explained.

FIG. 16 shows a first example of input/output of a trained model used in the generating function of FIG. 15, and an ultrasound diagnostic apparatus of an output destination. The processing circuitry 51 acquires ultrasound image data by the acquisition function 511. By the generating function 512, the processing circuitry 51 applies a trained model 73 to the ultrasound image data and generates an ultrasound imaging parameter relating to the ultrasound data. By the output function 513, the processing circuitry 51 outputs the ultrasound imaging parameter to an ultrasound imaging apparatus 74.

The ultrasound imaging parameter is a parameter relating to imaging of the ultrasound diagnostic apparatus when acquiring the ultrasound image data. Furthermore, the ultrasound imaging parameter may include information relating to the ultrasound diagnostic apparatus.

Examples of the ultrasound imaging parameter include the type of probe, a frame rate, a dynamic range, a frequency, and a flow velocity range. The frequency includes, for example, information on a center frequency of a transmission signal. The flow velocity range includes, for example, information on a flow velocity range in a color Doppler display.

Figure 17:
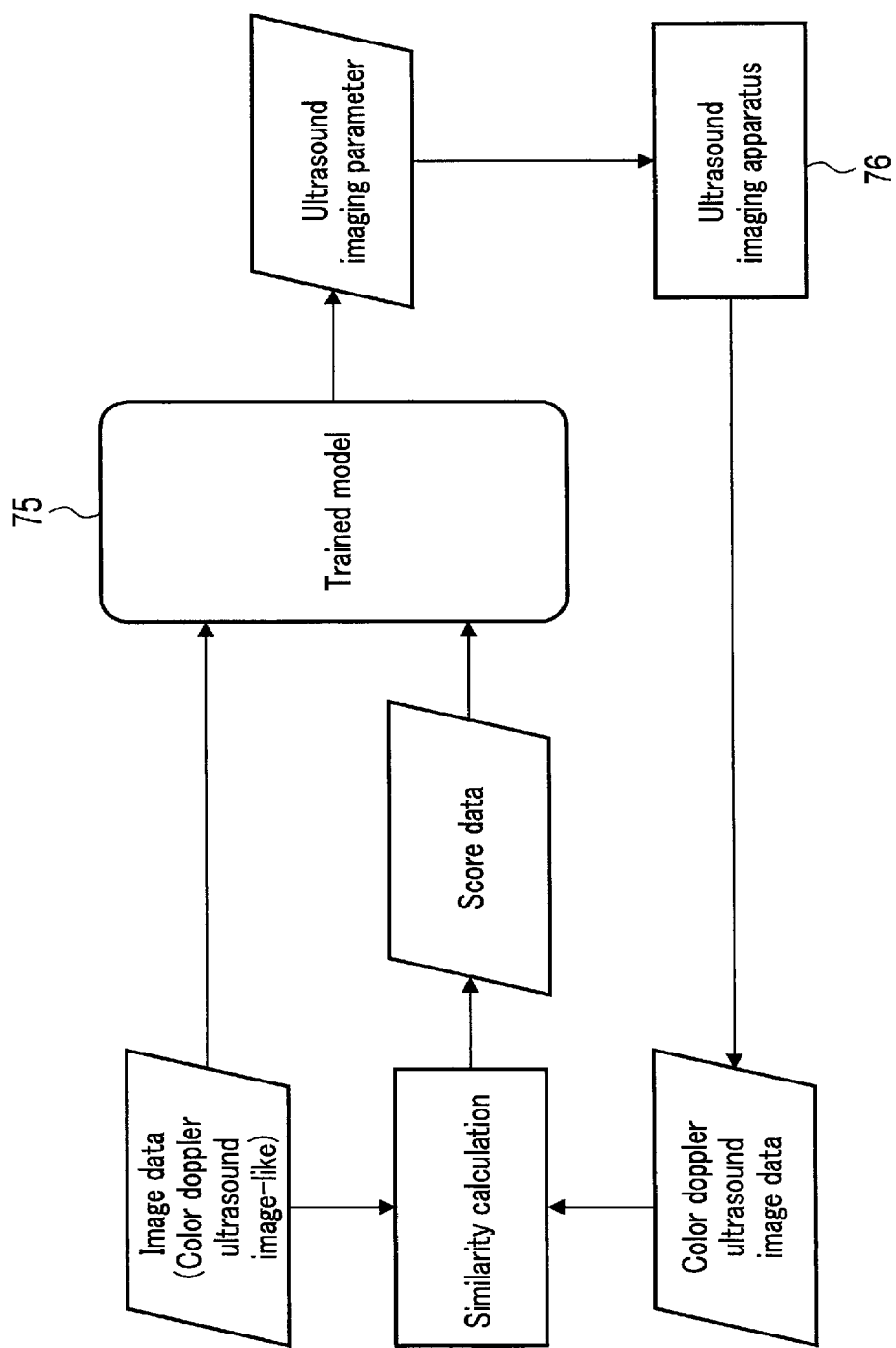
FIG. 17 shows a second example of input/output of a trained model used in a generating function of FIG. 16, an ultrasound diagnostic apparatus of an output destination, and a specific example of processing relating to input.

FIG. 17 shows a second example of input/output of the trained model used in the generating function of FIG. 16, an ultrasound diagnostic apparatus of an output destination, and a specific example of processing relating to input. In the example of FIG. 17, a display of an ultrasound image generated in real time can be optimized by generating an ultrasound imaging parameter based on color Doppler ultrasound image-like image data to be of reference, executing imaging based on the generated ultrasound imaging parameter, and feeding back information on ultrasound image data generated by the imaging to the generating processing of the ultrasound imaging parameter. Summarizing FIG. 17, the ultrasound diagnostic apparatus 1-3 is capable of performing feedback control in real time for the display of the ultrasound image by using the ultrasound image data generated by ultrasound imaging.

It should be noted that, in FIG. 17, although the color Doppler ultrasound image-like image data is input to a trained model 75, the data is not limited thereto, and may be the color Doppler ultrasound image data. Furthermore, the trained model 75 of FIG. 17 is capable of changing the weight of the model based on score data, and varying each value of the ultrasound imaging parameter.

Figure 18:
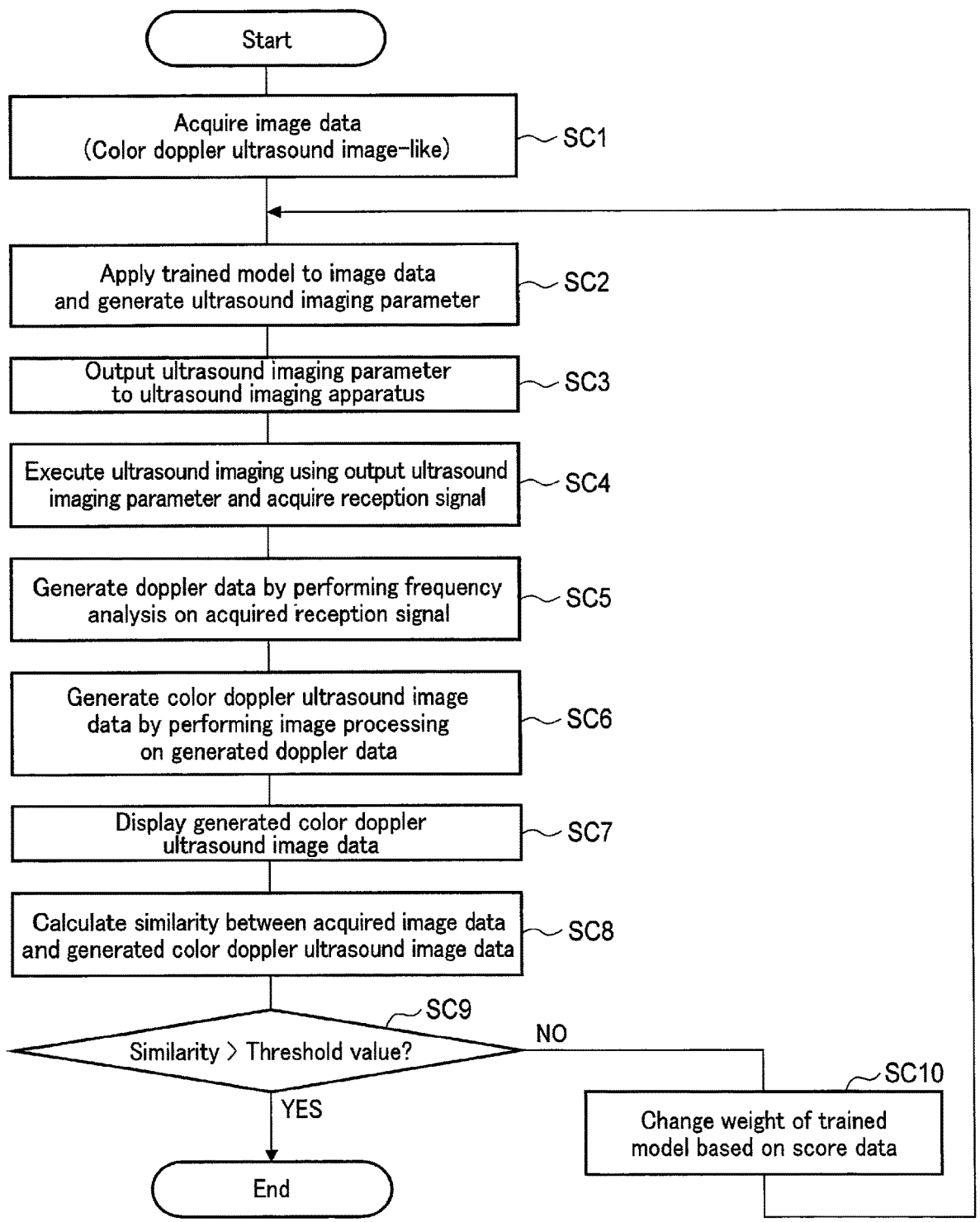
FIG. 18 is a flowchart for explaining a series of events including ultrasound imaging parameter estimation processing in the third embodiment relating to FIG. 17.

FIG. 18 is a flowchart for explaining a series of events including ultrasound imaging parameter estimation processing in the third embodiment relating to FIG. 17. For example, the flowchart of FIG. 18 starts by the processing circuitry 51 executing an ultrasound imaging parameter estimation program, which is triggered by an instruction to activate an application relating to the ultrasound imaging parameter estimation processing input by a user.

(Step SC1)
When the ultrasound imaging parameter estimation program is executed, the processing circuitry 51 executes the acquisition function 511. When the acquisition function 511 is executed, the processing circuitry 51 acquires color Doppler ultrasound image-like image data assigned by the user.

(Step SC2)
After acquiring the color Doppler ultrasound image-like image data, the processing circuitry 51 executes the generating function 512. When the generating function 512 is executed, the processing circuitry 51 applies the trained model 75 to the color Doppler ultrasound image-like image data and generates an ultrasound imaging parameter relating to the color Doppler ultrasound image-like image data. It should be noted that this ultrasound imaging parameter includes the flow velocity range.

(Step SC3)
After generating the ultrasound imaging parameter, the processing circuitry 51 executes the output function 513. When the output function 513 is executed, the processing circuitry 51 outputs the ultrasound imaging parameter to an ultrasound imaging apparatus 76. The ultrasound imaging apparatus 76 to be explained is assumed to be identical to the ultrasound diagnostic apparatus 1-3.

(Step SC4)
After receiving the ultrasound imaging parameter, the processing circuitry 51 executes the imaging control function. When the imaging control function is executed, the processing circuitry 51 executes ultrasound imaging using the ultrasound imaging parameter generated in step SC2, and acquires a reception signal.

(Step SC5)
After acquiring the reception signal, the processing circuitry 51 executes the Doppler mode processing function. When the Doppler mode processing function is executed, the processing circuitry 51 generates Doppler data by performing frequency analysis on the acquired reception signal.

(Step SC6)
After generating the Doppler data, the processing circuitry 51 executes the image processing function. When the image processing function is executed, the processing circuitry 51 generates color Doppler ultrasound image data by performing image processing on the generated Doppler data.

(Step SC7)
After the color Doppler ultrasound image data is generated, the processing circuitry 51 executes the display control function 514. When the display control function 514 is executed, the processing circuitry 51 displays the generated color Doppler ultrasound image data on the display 53. Furthermore, the processing circuitry 51 displays the color Doppler ultrasound image data based on the flow velocity range included in the ultrasound imaging parameter.

(Step SC8)
After the color Doppler ultrasound image data is displayed, the processing circuitry 51 executes the similarity calculation function. When the similarity calculation function is executed, the processing circuitry 51 calculates the similarity between the color Doppler ultrasound image-like image data acquired in step SC1 and the generated color Doppler ultrasound image data.

(Step SC9)
After the similarity is calculated, the processing circuitry 51 determines whether or not the calculated similarity is higher than a threshold value. In the case where the similarity is higher than the threshold value, it is determined that the display of a color Doppler ultrasound image generated in real time is optimized, and the processing is ended. In the case where the similarity is equal to or lower than the threshold value, it is determined that the display of the color Doppler ultrasound image generated in real time is not optimized, and the processing proceeds to step SC10.

(Step SC10)
After performing the processing relating to the determination of the similarity, the processing circuitry 51 executes the weight changing function. When the weight changing function is executed, the processing circuitry 51 changes the weight of the trained model 75 based on score data corresponding to the similarity. After step SC10, the processing returns to step SC2.

As explained above, the ultrasound diagnostic apparatus according to the third embodiment acquires ultrasound image data, and generates an ultrasound imaging parameter by inputting the ultrasound image data to a trained model, the ultrasound imaging parameter being a parameter of the ultrasound diagnostic apparatus with respect to the ultrasound image data, the trained model being trained to generate an ultrasound imaging parameter of the ultrasound diagnostic apparatus based on an ultrasound image data. Therefore, the ultrasound diagnostic apparatus according to the present embodiment is capable of estimating an ultrasound imaging parameter used for ultrasound imaging from ultrasound image data of which the ultrasound imaging parameter is unknown so that, for example, a user may set an optimal ultrasound imaging parameter.

Various types of imaging parameter estimation can be used for performing indexing processing with respect to medical data. As an example, a state in which a plurality of pieces of medical data are stored in a storage (for example, SSD, HDD, or a cloud storage) is considered. If the medical data is data that is imaged by a variety of imaging parameters, a user's request to search for only the related medical data in accordance with the purpose thereof may often occur. In order to efficiently refer to such medical data, processing referred to as indexing is often performed to add additional information such as an imaging parameter to the medical data in advance. By adding a parameter that is estimated using the imaging parameter estimation to the medical data held in the storage, when the user performs a search request, the related medical data can be output while referring to the estimation parameter. Furthermore, by performing indexing with respect to an image of a web site or a paper image, etc., using various types of imaging parameter estimation, a massive search of the related medical data would also be possible.

In addition, by using various types of imaging parameter estimation with respect to medical data that is not in DICOM format, such as an indexing Web site image or paper image, and outputting the result thereof as the DICOM format, the result can be captured in searchable form in a work station having a search function corresponding to the medical data in DICOM format.

According to at least one of the embodiments explained above, an optimal imaging parameter can be set.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical data processing apparatus, comprising processing circuitry configured to:
 acquire first medical image data for which a first imaging parameter by a magnetic resonance imaging apparatus is not known;
 input the first medical image data to a trained model, wherein the trained model is trained based on second medical image data and a second imaging parameter, the second medical image data is acquired by the magnetic resonance imaging apparatus, the second imaging parameter is used for acquiring the second medical image data by the magnetic resonance imaging apparatus; and
 generate, by the trained model, the first imaging parameter by which the first medical image data was acquired by the magnetic resonance imaging apparatus.

2. The medical data processing apparatus according to claim 1, wherein the processing circuitry is further configured to:
 acquire first supplementary data including a part of a parameter relating to the first medical image data, and
 generate the first imaging parameter by inputting the first medical image data and the first supplementary data to the trained model, the trained model being trained to generate the second imaging parameter based on second medical image data and second supplementary data, the second supplementary data being related to the second medical image data.

3. The medical data processing apparatus according to claim 2, wherein the first supplementary data and the second supplementary data are digital imaging and communication in medicine (DICOM) data.

4. The medical data processing apparatus according to claim 1, wherein the processing circuitry is further configured to:
 acquire first label data including information relating to a type of the first medical image data, and
 generate the first imaging parameter by inputting the first medical image data and the first label data to the trained model, the trained model being trained to generate the second imaging parameter based on second medical image data and second label data, the second label data being related to the second medical image data.

5. The medical data processing apparatus according to claim 1, wherein the first medical image data is associated with the magnetic resonance imaging apparatus.

6. The medical data processing apparatus according to claim 1, wherein the first medical image data is medical image-like image data obtained by photographing or reading a medical image printed on paper or recorded on film.

7. The medical data processing apparatus according to claim 6, wherein the medical image-like image data is associated with the magnetic resonance imaging apparatus.

8. The medical data processing apparatus according to claim 1, wherein the first medical image data is magnetic resonance image data.

9. The medical data processing apparatus according to claim 8, wherein the first imaging parameter includes a sequence of the magnetic resonance imaging apparatus.

10. The medical data processing apparatus according to claim 1, wherein the processing circuitry is further configured to:
 acquire map image data generated based on a plurality of pieces of medical image data, and
 generate a plurality of imaging parameters by inputting the map image data to the trained model, the plurality of imaging parameters being related to the plurality of pieces of first medical image data, the trained model being trained to generate a plurality of imaging parameters based on map image data generated based on a plurality of pieces of medical image data.

11. A magnetic resonance imaging apparatus, comprising:
 the medical data processing apparatus according to claim 1; and
 an imaging apparatus configured to perform medical imaging based on the first imaging parameter.

12. The magnetic resonance imaging apparatus according to claim 11, further comprising control circuitry configured to perform feedback control in real time by using medical image data generated by the medical imaging.

* * * * *